(12) United States Patent
Bollag et al.

(10) Patent No.: US 8,808,715 B1
(45) Date of Patent: Aug. 19, 2014

(54) METHODS AND COMPOSITIONS FOR MODULATING KERATINOCYTE FUNCTION

(75) Inventors: Wendy Bollinger Bollag, Martinez, GA (US); Xiaofeng Zhong, Augusta, GA (US); Xiangjian Zheng, Nashville, TN (US)

(73) Assignee: Georgia Regents Research Institute, Inc, Atlanta, GA (US)

( * ) Notice: Subject to any disclaimer, the term of this patent is extended or adjusted under 35 U.S.C. 154(b) by 996 days.

(21) Appl. No.: 12/164,021

(22) Filed: Jun. 28, 2008

Related U.S. Application Data

(63) Continuation-in-part of application No. 11/791,388, filed as application No. PCT/US2005/042748 on Nov. 23, 2005, now abandoned.

(60) Provisional application No. 60/635,565, filed on Nov. 23, 2004.

(51) Int. Cl.
  *A61K 8/02* (2006.01)
  *A61K 9/127* (2006.01)

(52) U.S. Cl.
  USPC .......................................... 424/401; 424/450

(58) Field of Classification Search
  None
  See application file for complete search history.

(56) References Cited

U.S. PATENT DOCUMENTS

| | | | | |
|---|---|---|---|---|
| 4,755,388 A | * | 7/1988 | Heath et al. | 424/450 |
| 4,944,948 A | | 7/1990 | Uster et al. | |
| 5,246,708 A | | 9/1993 | von Borstel et al. | |
| 5,510,120 A | * | 4/1996 | Jones et al. | 424/499 |
| 5,716,638 A | | 2/1998 | Touitou | |
| 5,851,543 A | * | 12/1998 | Korb et al. | 424/401 |
| 2006/0039978 A1 | * | 2/2006 | Diederichs | 424/484 |

FOREIGN PATENT DOCUMENTS

| | | | |
|---|---|---|---|
| WO | 90/11781 | * | 10/1990 |
| WO | 01/19403 | * | 3/2001 |

OTHER PUBLICATIONS

Falk et al. Eur. J. Surg., 2001, vol. 167, pp. 136-141.*
Yokomizo et al. Journal of Controlled Release, 1996, vol. 42, pp. 37-46.*
International Search Report, Patent Cooperation Treaty, Jul. 1, 2008.
Canadian Intellectual Property Office, office action, Jul. 2, 2010.
Xiangjian Zheng and Wendy Bollinger Bollag, J. Invest. Dermatol., v.121(6) 1487-1495 (Dec. 6, 2003).
Xiangjian Zheng, Sagarika Ray, and Wendy B. Bollag, Modulation of phospholipase D-mediated phosphatidylglycerol formation by differentiating agents in primary mouse epidermal keratinocytes, Biochimica et Biophysica Acta (BBA)—Molecular Cell Research, vol. 1643, Issues 1-3, Dec. 7, 2003, pp. 25-36.

* cited by examiner

*Primary Examiner* — Anand Desai
*Assistant Examiner* — Melissa Mercier
(74) *Attorney, Agent, or Firm* — Pabst Patent Group LLP

(57) ABSTRACT

The disclosure is generally directed to methods and compositions for modulating keratinocyte function, more particularly, to compositions and methods for normalizing keratinocyte proliferation and differentiation, compositions and methods for modulating levels of phosphatidylglycerol (PG) in keratinocytes, and compositions and methods for treating skin conditions by modulating keratinocyte proliferation.

12 Claims, 25 Drawing Sheets

A

[Glycerol or Propylene Glycol]
(equivalent volume percent)

B

Glycerol    Propylene Glycol

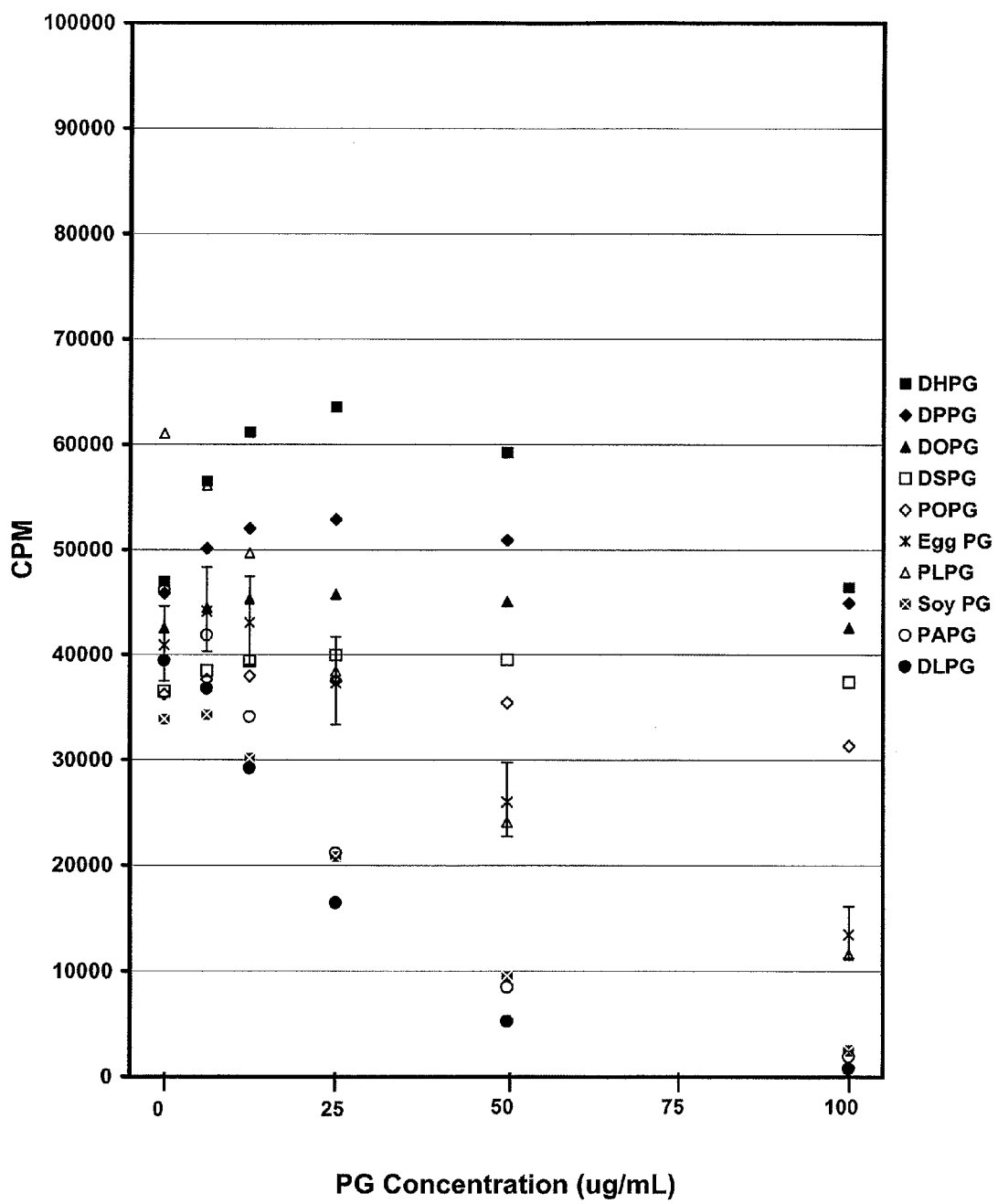

METHODS AND COMPOSITIONS FOR MODULATING KERATINOCYTE FUNCTION

CROSS-REFERENCE TO RELATED APPLICATION

This application is a continuation-in-part of U.S. application Ser. No. 11/791,388, which is the National Stage of International Application No. PCT/US2005/042748, filed Nov. 23, 2005, which claims the benefit of U.S. Provisional Application No. 60/635,565, filed Nov. 23, 2004 each of which are entirely incorporated herein by reference.

STATEMENT REGARDING FEDERALLY SPONSORED RESEARCH OR DEVELOPMENT

Aspects of this disclosure were supported in part by the National Institutes of Health Grant Nos. AR45212 and AR55022. The United States Government may have certain rights with respect to the claimed subject matter.

FIELD OF THE DISCLOSURE

The disclosure is generally directed to methods and compositions for modulating keratinocyte function, more particularly, to compositions and methods for normalizing keratinocyte proliferation and differentiation.

BACKGROUND

The skin is the largest organ of the body and is composed of the epidermis and dermis. The most important function of the skin is to provide the essential physical and water permeability barrier. The epidermis is a continuously regenerating tissue, which differentiates to produce a mechanical and water permeability barrier, thus making possible a terrestrial existence. This barrier is established in the epidermis by a precisely regulated keratinocyte differentiation program that results in distinct epidermal layers. The structure of the epidermis is maintained by a finely tuned balance between keratinocyte proliferation and differentiation, which results in a multilayer structure consisting of basal, spinous, granular, and cornified layers.

The innermost basal layer, which is in contact with the basement membrane, is composed of a single layer of undifferentiated keratinocytes with proliferative potential. The spinous layer consists of non-proliferating keratinocytes in an early differentiation stage with progressive maturation as the cells move from suprabasal layers outward. Spinous differentiation is followed by late differentiation in the granular layer and terminal differentiation in the outermost cornified layer (see FIG. 1). Once committed to differentiation, the cells in the basal layer lose their proliferative potential and move toward the terminally differentiated cornified layer. Despite intense investigation and data implicating elevated extracellular calcium levels, 1,25-dihydroxyvitamin $D_3$ and other molecules, the exact mechanisms by which the keratinocyte differentiation process is initiated and regulated remain unclear.

The precise regulation of differentiation in the epidermis is crucial for proper stratification and barrier formation to occur. Epidermal homeostasis is maintained in part by orchestrating the correct expression of genes in keratinocytes at each stage of differentiation. Alterations in this differentiation program can result in skin disorders, such as psoriasis, eczema, atopic dermatitis, skin cancers, such as squamous and basal cell carcinoma, and other conditions of the skin characterized by unregulated cell division.

Thus, any upset in the balance of skin cell proliferation and differentiation signals can result in various disorders or other undesirable skin conditions. While an over-stimulation of keratinocyte proliferation may lead to hyperproliferative skin conditions, such as those mentioned above (i.e. psoriasis and various non-melanoma skin cancers), under-stimulation of keratinocyte proliferation may result in a situation of reduced growth, such as that characterized by aging skin (skin cell senescence) or skin that has been damaged. Thus, treatments directed at reducing and/or inhibiting proliferation of keratinocytes would be useful for treating conditions characterized by hyperproliferation of skin cells. Likewise, treatments for increasing proliferation of keratinocytes would be useful to improve the condition of aging or damaged skin, where new growth is slowed, and/or to accelerate wound healing. Particularly beneficial treatments would provide the ability to treat both conditions simultaneously or as needed; however no such treatments are currently available.

Accordingly, there is a need for new and effective treatments for conditions and/or diseases related to an over- or under-proliferation of skin cells. There is also a need for ways to modulate keratinocyte proliferation and/or behavior. In particular, there is a need for new methods and treatments to normalize keratinocyte proliferation.

SUMMARY

Briefly described, the present disclosure provides methods and compositions for normalizing keratinocyte function and/or proliferation. Aspects of the present disclosure also include modulating keratinocyte function, and/or modulating levels of phosphatidylglycerol (PG), or a functional derivative thereof, in keratinocytes. In addition, the present disclosure provides methods and compositions for treating skin conditions by modulating keratinocyte proliferation.

Accordingly, embodiments of methods according to the present disclosure for modulating keratinocyte function include modifying the amount of PG, or a functional derivative thereof, in keratinocytes. Other embodiments include methods for modulating keratinocyte function including contacting a keratinocyte with an amount of PG, a functional derivative thereof, a prodrug of the any of the foregoing or a pharmaceutically acceptable salt of the any of the foregoing, effective to modulate signal transduction in the keratinocyte. Embodiments of methods of modulating production of phosphatidic acid and PG include contacting keratinocytes with a non-glycerol based alcohol.

Further, embodiments of the present disclosure for treating a skin condition include administering to a host an amount of PG, a functional derivative thereof, a prodrug of the any of the foregoing or a pharmaceutically acceptable salt of the any of the foregoing, in an amount effective to treat the skin disorder. Other embodiments of treating a skin condition in a host include increasing the amount of PG in host keratinocytes. Methods of treating a skin condition in a host also include administering to the host an amount of PG effective to treat the skin condition, wherein the PG stimulates skin cell proliferation when the skin condition is characterized by under-proliferation of skin cells, and inhibits skin cell proliferation when the skin condition is characterized by over-proliferation of skin cells.

Embodiments of methods of normalizing keratinocyte proliferation in a host include administering to the host an effective amount of PG, a functional derivative thereof, a prodrug of the any of the foregoing or a pharmaceutically acceptable salt of the any of the foregoing, wherein the foregoing stimulates keratinocyte proliferation under conditions of reduced proliferation, and wherein the foregoing inhibits keratinocyte proliferation under conditions of over-proliferation. The present disclosure also provides methods of accelerating wound healing in a host including increasing the amount of PG or a functional derivative thereof in host keratinocytes.

The present disclosure also provides compositions for treating various skin conditions. Embodiments of compositions of the present disclosure include an amount of PG, a functional derivative thereof, a prodrug of the any of the foregoing or a pharmaceutically acceptable salt of the any of the foregoing, effective to modulate skin cell signal transduction. Other embodiments of compositions of present disclosure include an amount of liposomes of PG, a functional derivative thereof, a prodrug of the any of the foregoing or a pharmaceutically acceptable salt of the any of the foregoing effective to modulate skin cell signal transduction.

Other systems, methods, features, and advantages of the present disclosure will be or will become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure.

DETAILED DESCRIPTION

Figure 1:
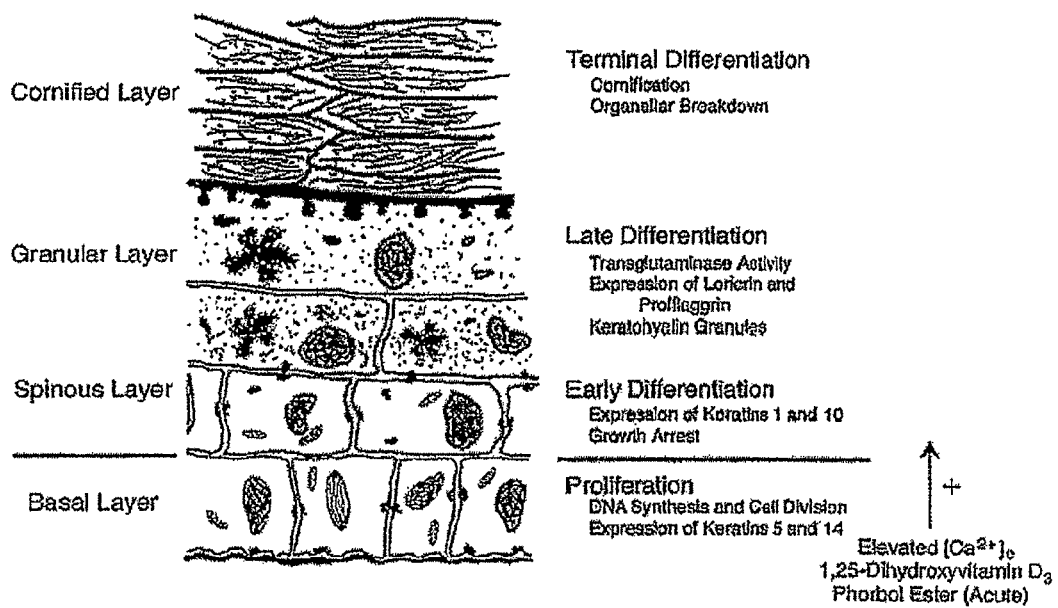
FIG. 1 is an illustration of the layers of the skin and the stages of proliferation and differentiation of keratinocytes.

Embodiments of the present disclosure will employ, unless otherwise indicated, techniques of synthetic organic chemistry, biochemistry, molecular biology, and the like, which are within the skill of the art. Such techniques are explained fully in the literature. The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

As used herein, the term "host" or "organism" includes both humans, mammals (e.g., cats, dogs, horses, etc.), and other living species that are in need of treatment for conditions/diseases of the skin. A living organism can be as simple as, for example, a single eukaryotic cell or as complex as a mammal. Further, a "composition" can include one or more chemical compounds, as described below.

As used herein, the term "derivative" refers to a modification to the disclosed compounds including, but not limited to, hydrolysis, reduction, or oxidation products, of the disclosed compounds. Hydrolysis, reduction, and oxidation reactions are known in the art.

As used herein, the term "functional derivative" refers to a derivative of the disclosed compounds that retains the function of the disclosed compound, at least in part. For instance, in the case of PG, a functional derivative of PG in the context of the present disclosure includes a derivative of PG which has the effect of modulating skin cell signal transduction and/or proliferation. A non-limiting example of a functional derivative of PG in the present disclosure is the phosphatidylalcohol formed upon transphosphatidylation using propylene glycol or 1-propanol, which has the same chemical structure of PG minus one or two hydroxyl groups, respectively, and which retains the activity of PG, at least in part.

As used herein, the term "therapeutically effective amount" refers to that amount of the compound being administered which will relieve to some extent one or more of the symptoms caused directly or indirectly by an over- or under-proliferation of keratinocytes. In reference to conditions/diseases caused directly or indirectly by an over- or under-proliferation of keratinocytes, a therapeutically effective amount refers to that amount which has the effect of preventing the condition/disease from occurring in an animal that may be predisposed to the disease but does not yet experience or exhibit symptoms of the condition/disease (prophylactic treatment), alleviation of symptoms of the condition/disease, diminishment of extent of the condition/disease, stabilization (i.e., not worsening) of the condition/disease, preventing the spread of condition/disease, delaying or slowing of the condition/disease progression, amelioration or palliation of the condition/disease state, and combinations thereof.

As used herein, the term "pharmaceutically acceptable salt" refers to those salts that retain the biological effectiveness and properties of the free bases and which are obtained by reaction with inorganic or organic acids such as, but not limited to, hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

As used herein, the term "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

As used herein, the term "excipient" refers to an inert substance added to a pharmaceutical composition to further facilitate administration of a compound. Examples of excipients include, but are not limited to, calcium carbonate, calcium phosphate, various sugars and types of starch, cellulose derivatives, gelatin, vegetable oils, and polyethylene glycols.

As used herein, "treat," "treating," and/or "treatment" are an approach for obtaining beneficial or desired clinical results. For purposes of embodiments of this disclosure, beneficial or desired clinical results include, but are not limited to, preventing the condition/disease from occurring in an animal that may be predisposed to the condition/disease but does not yet experience or exhibit symptoms of the disease (prophylactic treatment), alleviation of symptoms of the condition/disease, diminishment of extent of the condition/disease, stabilization (i.e., not worsening) of the condition/disease, preventing spread of the condition/disease, delaying or slowing of the condition/disease progression, amelioration or palliation of the condition/disease state, and combinations thereof, hi addition, "treat", "treating", and "treatment" can also mean prolonging survival as compared to expected survival if not receiving treatment.

As used herein, the term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. ScL; E. B. Roche, ed. (1977). Bioreversihle Carriers in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 1 1,:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990). Prodrugs for the improvement of drug absorption via different routes of administration, Eur. J. DrugMetab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenyloin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985). Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sd., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. DrugMetab., 1(1):31-48; D. M. Lambert (2000). Rationale and applications of lipids as prodrug carriers, Eur. J. Pharm. ScL, 11 Suppl 2:S15-27; Wang, W. et al. (1999). Prodrug approaches to the improved delivery of peptide drugs. Curr. Pharm. Des., 5(4):265-87.

As used herein, the term "topically active agents" refers to compositions of the present disclosure that elicit pharmacological responses at the site of application (contact) to a host.

As used herein, the term "topically" refers to application of the compositions of the present disclosure to the surface of the skin and mucosal cells and tissues.

As used herein, the term "inhibit," "suppress," "decrease," "interfere," and/or "reduce" (and like terms) generally refers to the act of reducing, either directly or indirectly, a function, activity, or behavior relative to the natural, expected, or average or relative to current conditions. For instance, something that inhibits, suppresses, decreases or reduces or interferes with keratinocyte proliferation might stop or slow the growth of new keratinocytes.

As used herein, the term "increase," "enhance," "stimulate," and/or "induce" (and like terms) generally refers to the act of improving or increasing, either directly or indirectly, a function or behavior relative to the natural, expected, or average or relative to current conditions. For instance, something that increases, stimulates, induces or enhances keratinocyte proliferation might induce proliferation of keratinocytes that have slowed or stopped proliferating or accelerate the rate of proliferation over the normal rate.

As used herein, the term "modulate," "modify," and/or "modulator" generally refers to the act of directly or indirectly promoting/stimulating or interfering with/inhibiting a specific function or behavior. For instance, a modulator of keratinocyte function might stimulate or increase keratinocyte proliferation or differentiation, or a modulator of keratinocyte function might inhibit or decrease keratinocyte proliferation or differentiation. In some instances a modulator may increase and/or decrease a certain activity or function relative to its natural state or relative to the average level of activity that would generally be expected or relative to a current level of activity.

As used herein, the term "normalize" refers to the act of establishing and/or maintaining a relative balance or equilibrium between two or more activities, functions or conditions. For instance to normalize keratinocyte proliferation generally refers to maintaining a relative balance between keratinocyte proliferation and differentiation under various conditions. Under conditions of over-proliferation, to normalize might mean to slow or inhibit proliferation, while under conditions of slowed growth, to normalize might mean to induce or increase proliferation.

As used herein, the term "expression" refers to the process undergone by a structural gene to produce a polypeptide. It is a combination of transcription and translation. Thus, to induce or increase expression of PLD2 or AQP3 refers to increasing or inducing the production of the PLD2 or AQP3 polypeptide, which may be done by a variety of approaches, such as increasing the number of genes encoding for the polypeptide, increasing the transcription of the gene (such as by placing the gene under the control of a constitutive promoter), or increasing the translation of the gene, or a combination of these and/or other approaches.

As used herein, the terms "including", "such as", "for example" and the like are intended to refer to exemplary embodiments and not to limit the scope of the present disclosure.

General Discussion
Phospholipase D

Figure 2:
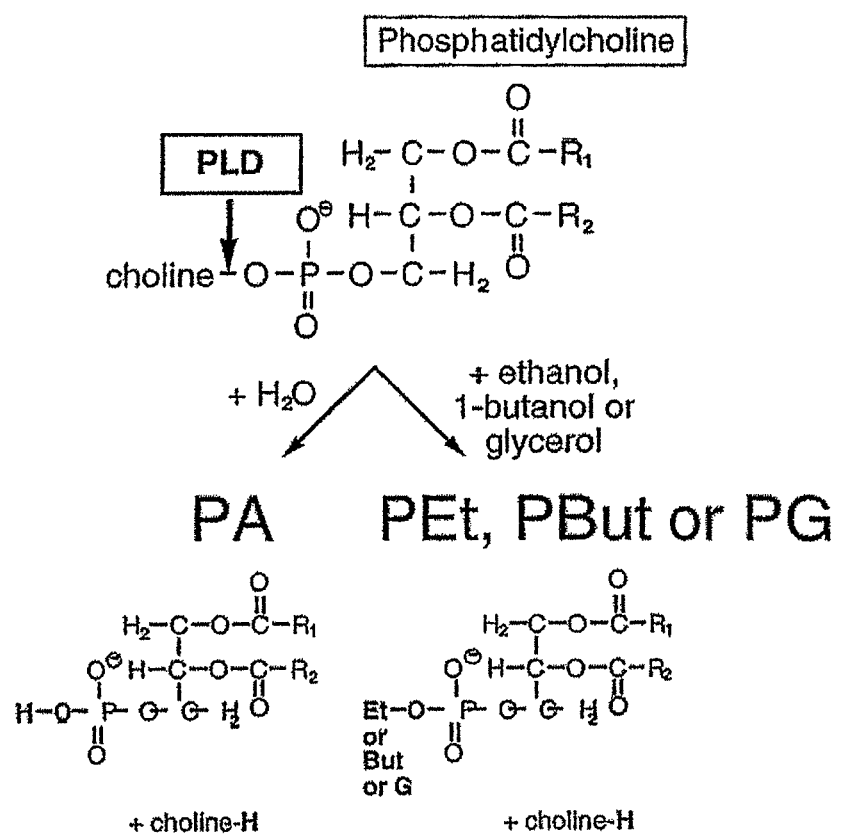
FIG. 2 illustrates the transphosphatidylation reaction of PLD. In the presence of water, PLD catalyzes the hydrolysis of the phospholipid phosphatidylcholine to yield phosphatidic acid (PA) and choline. However, in the presence of small amounts of a primary alcohol such as ethanol, 1-butanol, or glycerol, PLD catalyzes a transphosphatidylation reaction to produce the corresponding phosphatidylalcohol.

Phospholipase D (PLD) is a lipolytic enzyme that has been implicated in multiple cellular processes including growth, differentiation, vesicle trafficking and cytoskeletal rearrangement. PLDs catalyze the hydrolysis of phosphatidylcholine to generate phosphatidic acid (PA) and choline. PA and its metabolites, diacylglycerol and lysophosphatidic acid, are involved in multiple physiological events. In the presence of primary alcohols, PLD can also catalyze the transphosphatidylation reaction to generate phosphatidylalcohols. Pursuant to this mechanism, PLD can metabolize phosphatidylcholine in the presence of a physiological primary alcohol glycerol to yield phosphatidylglycerol (PG); other primary alcohols may also be used in this reaction, such as propylene glycol or 1-propanol, to yield similar products. The reactions of PLD are illustrated in FIG. 2.

Figure 3:
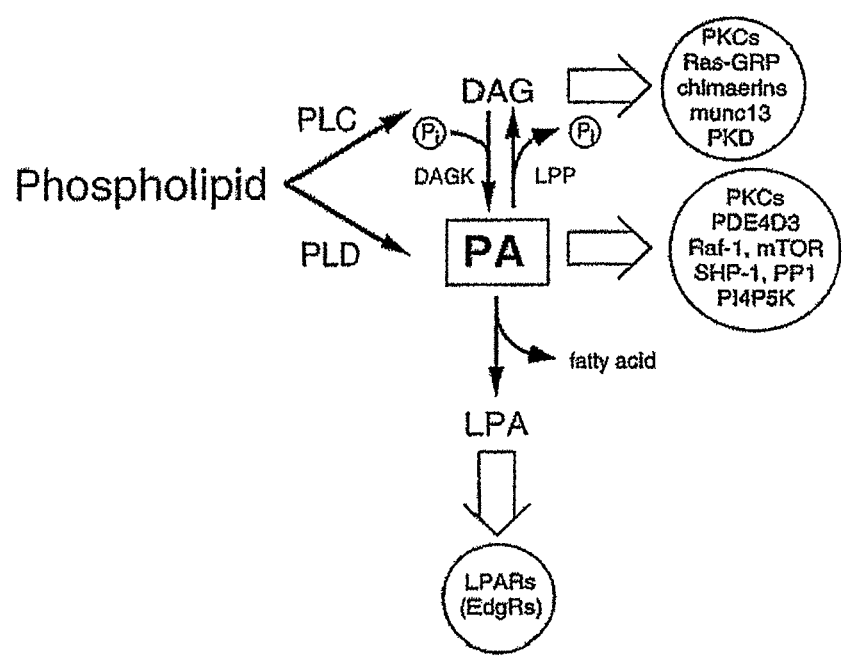
FIG. 3 illustrates PLD signaling pathways, including regulation, signal generation, and effector enzymes.
Figure 4:
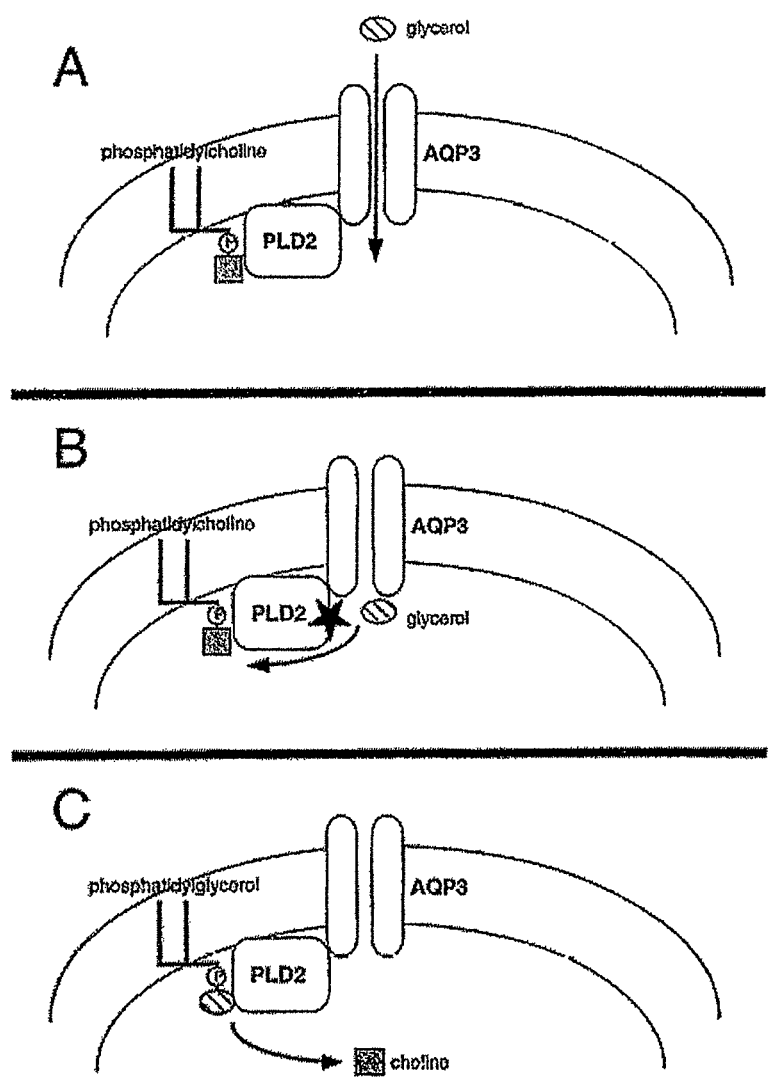
FIG. 4 is a model of the AQP3-PLD2-glycerol-phosphatidylglycerol signaling module.

Two isoforms of mammalian PLD, PLD1 and PLD2, have been identified. PLD1 has a low basal activity and is activated by small G proteins (Arf, Rho, and Rac) and protein kinase C, whereas PLD2 appears to be constitutively active, as demonstrated by transfection into insect cells monitored in vitro. Both PLDs use phosphatidylinositol 4,5-bisphosphate ($PIP_2$) as a cofactor and have been shown to be expressed in keratinocytes. 1,25-Dihydroxyvitamin $D_3$, a keratinocyte differentiating agent, induces PLD1, but not PLD2 expression. FIG. 3 illustrates various signaling pathways of PLD. In HaCaT cells, PLD2 has been located in caveolin-rich membrane microdomains.

The location of PLD2 and its ability to produce phosphatidylglycerol (PG) implicates PLD2 in the modulation of keratinocyte behavior, specifically with respect to signal transduction for regulating keratinocyte proliferation and differentiation, as will be discussed in greater detail below.

Aquaporin 3

Aquaporins (AQP) are a family of small transmembrane water and/or glycerol channels. Currently, eleven mammalian aquaporins (AQP0-10) have been identified and characterized. According to their structural and functional properties, aquaporins can be divided into two subgroups: "aquaporins", which transport only water, and "aquaglyceroporins", which can transport both water and glycerol. AQP3, which belongs to the aquaglyceroporin subgroup, is a relatively weak transporter of water but an efficient transporter of glycerol. AQP3 is expressed in kidney collecting cells, red cells, dendritic cells and epithelial cells from a variety of tissues including the urinary, digestive, and respiratory tracts and the epidermis. In epidermal, tracheal and nasopharyngeal epithelium, AQP3 is present in basal cells of the epidermis.

AQP3-deficient mice display selectively reduced glycerol content, as well as decreased water holding capacity, in the epidermis, impaired skin elasticity, delayed barrier recovery after stratum corneum removal and delayed wound healing, suggesting a role of AQP3 in regulating keratinocyte proliferation and differentiation. This phenotype can be corrected by topical or oral application of glycerol but not other osmotically active molecules, suggesting that the effect is not simply a function of glycerol's hydrophilic properties. AQP3's ability to transport glycerol, which can be used to produce PG as discussed above, and its location, discussed below, indicate a role for AQP3 in the modulation of PG production and keratinocyte function, which will be discussed in greater detail below.

PLD2/AQP3/Glycerol/PG Signaling Module

The inventors of the present disclosure have previously shown that in keratinocytes AQP3 and PLD2 associate in caveolin-rich membrane microdomains and that the presence of the AQP3 glycerol channel is important for normal epidermal function (Zheng, X. and Bollag, W. B. (2003) J. Invest. Dermatol, 121, 1487-1495, which is hereby incorporated by reference). Caveolae are a subset of lipid raft microdomains, which are characterized electron microscopically as flask-shaped invaginations of 50-100 nm diameter in the plasma membrane. Caveolin 1 is the first structural protein component identified in caveolae and has been functionally implicated in a wide variety of signal transduction processes (Smart et al., 1999). In addition, caveolin 1 has recently been shown to associate with lamellar bodies in keratinocytes (Sando et al., 2003).

The colocation of AQP3 with PLD2 in caveolin-rich membrane microdomains suggests that AQP3 transports glycerol to PLD2 for use in the transphosphatidylation reaction to produce PG and that PG, in turn, acts as a lipid second messenger to modulate keratinocyte function, which is further demonstrated by Examples 1 and 2, below. Indeed, the Examples herein demonstrate the existence of a novel signaling module comprised of AQP3, PLD2, glycerol and PG.

Example 2 also demonstrates that direct provision of PG liposomes inhibited DNA synthesis in a dose-dependent fashion in rapidly dividing keratinocytes, although in growth-inhibited cells, PG liposomes dose-dependently enhanced [$^3$H] thymidine incorporation into DNA. A trend for stimulation of transglutaminase activity by PG liposomes was also observed. These data support that a signaling module consisting of AQP3, PLD2, glycerol and PG is involved in promoting growth inhibition and/or early differentiation of proliferating keratinocytes or promoting growth stimulation in growth inhibited keratinocytes, thereby providing a mechanism for modulating keratinocyte behavior and/or proliferation and methods for treating various skin conditions characterized by an increase or decrease in keratinocyte proliferation.

Methods of Modulating Keratinocyte Proliferation and Treating Skin Conditions

Embodiments of the present disclosure include methods of modulating keratinocyte function, particularly proliferation, by modulating the amounts and/or activities of the various components of the PLD2/AQP3/glycerol/PG signaling module. In certain embodiments of the present disclosure, keratinocyte proliferation is normalized by modulating the amount of PG, or a functional derivative thereof, produced by or in contact with keratinocytes. In embodiments of the present disclosure, modulating the amount of PG, or a functional derivative thereof, in contact with or produced by, keratinocytes normalizes keratinocyte proliferation by stimulating skin cell proliferation in conditions of slowed growth or under-proliferation of skin cells and inhibiting or decreasing skin cell proliferation under conditions of increased growth or hyperproliferation.

Some embodiments of modulating the amount of PG in contact with keratinocytes include increasing the amount of PG, a functional derivative thereof, a prodrug or a pharmaceutically acceptable salt of any of the foregoing, in contact with keratinocytes. Example functional derivatives of PG include, but are not limited to, the transphosphatidylation reaction product of other primary alcohols such as propylene glycol and 1-propanol, which has the same structure as PG, minus one and two hydroxy groups, respectively. Included within the meaning of PG or a functional derivative of PG are those species that contain selected fatty acid molecules at the $R_1$ and $R_2$ positions. In one embodiment, the fatty acid molecules are saturated, monounsaturated (containing one unsaturated bond) or polyunsaturated (containing two or more unsaturated bonds). The nature of the fatty acid molecules at the positions may be the same or may be different. In one embodiment, the fatty acid molecules contain from 4-28 carbon atoms and from 0-6 unsaturated bonds. Exemplary fatty acid molecules, include, but are not limited to, butyric (4:0), valeric (5:0), caproic (6:0), caprylic (8:0), capric (10:0), lauric (12:0), myristic (14:0), myristoleic (14:1, cis-9), palmitic (16:0), palmitoleic (16:1, 9-cis), stearic (18:0), oleic (18:1, 11-cis), vaccenic (18:1, 11-trans), linoleic (18:2, 9-cis, 12-cis), γ-linolenic (18:3, 6-cis, 9-cis, 12-cis), α-linolenic (18:3, 9-cis, 12-cis, 15-cis), arachidic (20:0), arachidonic (20:4, 5-cis, 8-cis, 11-cis, 14-cis), eicosapentaenoic (20:5, 5-cis, 8-cis, 11-cis, 14-cis, 17-cis), behenic (22:0), erucic (22:1, 13-cis), docosahexaenoic (22:6, 4-cis, 7-cis, 10-cis, 13-cis, 16-cis, 19-cis), lignoceric (24:0) and cerotic (26:0). In a particular embodiment, the PG molecule or functional derivative thereof contains at least one fatty acid with at least one unsaturated bond, such as but not limited to oleic or linoleic.

Embodiments of increasing the amount of PG in contact with keratinocytes to modulate keratinocyte behavior include, contacting keratinocytes with an amount of PG, a functional derivative thereof or a prodrug or a pharmaceutically acceptable salt of any of the foregoing effective to modulate keratinocyte proliferation, keratinocyte skin cell signal transduction, and/or keratinocyte nucleic acid synthesis. The examples below demonstrate that the PG acts to modulate signal transduction in the keratinocyte, which can increase or decrease nucleic acid synthesis in the keratinocyte, depending on various conditions.

A surprising and beneficial aspect of the present disclosure is that PG exhibits biphasic action in keratinocytes, inducing signals for proliferation under conditions of slowed growth, such as aging (i.e. cell senescence) or damage to skin cells, such as from exposure to unfavorable conditions (e.g. smoke, sun, wind, and extreme temperatures) or physical injury (such as wounds, burns, scrapes, scars, ulcers, etc.), and inducing signals to inhibit or slow proliferation under conditions of increased or hyper-proliferative growth, such as in disorders including, but not limited to, psoriasis, eczema, actinic keratosis, atopic dermatitis, basal cell carcinoma, and other non-melanoma skin cancers. Thus, rather than treating conditions of over- or undergrowth separately, the conditions can be addressed simultaneously by modulating PG levels and/or production, and or otherwise modulating the PLD2/AQP3/glycerol/PG signaling module.

Methods of the present disclosure are not limited to modulating PG levels by the administration of PG or primary alcohol, such as but not limited to, glycerol to keratinocytes or a host, but also include methods of modulating the amount of PG produced by keratinocytes. Embodiments of modulating the amount of PG produced by keratinocytes include modulating the activity of PLD, such as but not limited to, phospholipase D2 (PLD2) and/or AQP, such as but not limited to, aquaporin-3 (AQP3), for example by up-regulating or down-regulating the activity of such polypeptides and/or increasing or decreasing the expression of such polypeptides in keratinocytes. Embodiments for increasing the expression of PLD and/or AQP, such as but not limited to, PLD2 or AQP3, include increasing or inducing the production of the such polypeptide, which may be done by a variety of approaches known to those of skill in the art, non-limiting examples of which are disclosed below in the Examples. In general, approaches for increasing expression of polypeptides such as PLD2 or AQP3 include methods such as increasing the number of genes encoding for the polypeptide (such as by transfection of host cells with additional copies of the gene, by various methods known to those of skill in the art of gene therapy), increasing the transcription of the gene (such as by placing the gene under the control of a constitutive promoter), or increasing the translation of the gene, or a combination of these and/or other approaches.

Embodiments of the present disclosure also provide methods and compositions for treating skin conditions/disorders in a host characterized by over- or under-proliferation of keratinocytes by normalizing and/or modulating keratinocyte proliferation and/or function. Skin conditions treatable by methods and compositions of the present disclosure include, but are not limited to hyper-proliferative disorders such as psoriasis, eczema, actinic keratosis, atopic dermatitis, basal cell carcinoma, non-melanoma skin cancer, and unregulated cell division; conditions of slowed growth such as aging, scarring, skin cell senescence, and skin cell damage due to exposure (such as to sun, smoke, wind, extreme temperatures, etc.); and physical wounds (such as lacerations, ulcers such as diabetic and age-related ulcers, burns, scrapes, and the like).

Methods of treating the above conditions include, among others, the methods of modulating/normalizing, keratinocyte proliferation and/or function described above. In particular, embodiments of methods for treating the above conditions include administering an amount of PG, a functional derivative thereof, or a prodrug or a pharmaceutically acceptable salt of any of the foregoing effective to modulate keratinocyte proliferation, keratinocyte skin cell signal transduction, and/or keratinocyte nucleic acid synthesis. Methods of the present disclosure for modulating keratinocyte behavior and/or treating skin conditions may also include, in combination with the administration of PG, contacting keratinocytes with glycerol or a functional derivative thereof, as described below, to stimulate the cellular production of PG or functional derivatives of PG. Methods of the present disclosure also include contacting keratinocytes with a non-glycerol based alcohol to modulate the production of phosphatidic acid, PA, as well as PG as discussed in greater detail below. Embodiments of the present disclosure also include methods of treating the above conditions and modulating keratinocyte function and proliferation by administering a pharmaceutical composition of the present disclosure to a host in need thereof. Pharmaceutical compositions according to the present disclosure are described in greater detail below.

Pharmaceutical Compositions

Embodiments of pharmaceutical compositions and dosage forms of the present disclosure include PG, a pharmaceutically acceptable salt of PG or a functional derivative thereof, or a pharmaceutically acceptable polymorph, solvate, hydrate, dehydrate, co-crystal, anhydrous, or amorphous form thereof. Embodiments of the pharmaceutical compositions of the present disclosure may also include glycerol or a functional derivative thereof. Since glycerol acts as a substrate of PLD2 for the production of PG, glycerol has the additional effect of down-regulating phosphatidic acid (PA), which, as demonstrated in the Examples below, may also play a role in keratinocyte modulation.

Functional derivatives of glycerol, including but not limited to propylene glycol, have the same or similar effect as glycerol, in both increasing production of a PG functional derivative and in down-regulating the production of PA.

Other embodiments of compositions of the present disclosure may include nonfunctional derivatives of glycerol, such as other primary, non-glycerol based alcohols (e.g. 1-butanol and ethanol) that down-regulate PLD2 production of both PG and PA, as demonstrated in the examples below. Such compositions may or may not also include PG, depending on the desired effect. Compositions including a non-glycerol based alcohol without PG can inhibit/reduce the production of PA and PG, while compositions including a non-glycerol based alcohol and PG can inhibit/reduce PA production and induce PG-mediated modulation of keratinocyte behavior.

Pharmaceutical compositions and unit dosage forms typically also include one or more pharmaceutically acceptable excipients or diluents. Advantages provided by the active composition, such as, but not limited to, increased solubility and/or enhanced flow, purity, or stability (e.g., hygroscopicity) characteristics can make them better suited for pharmaceutical formulation and/or administration to patients than the prior art. Pharmaceutical unit dosage forms of the active composition are suitable for topical, transdermal, oral, mucosal (e.g., nasal, sublingual, vaginal, buccal, or rectal), or parenteral (e.g., intramuscular, subcutaneous, intravenous, intraarterial, or bolus injection) administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the active composition can vary depending on their use. For example, a dosage form used in the acute treatment of a disease or disorder may contain larger amounts of the active ingredient (e.g., the active composition) than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. (e.g., Remington's Pharmaceutical Sciences, 18th ed., Mack Publishing, Easton, Pa. (1990)).

Typical pharmaceutical compositions and dosage forms can include one or more excipients. Suitable excipients are well known to those skilled in the art of pharmacy or pharmaceutics. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form.

The disclosure further encompasses pharmaceutical compositions and dosage forms that include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts and specific type of active ingredient in a dosage form may differ depending on factors such as, but not limited to, the route by which it is to be administered to patients, the condition to be treated, the size of the host, etc. However, typical dosage forms of the compounds of the disclosure include PG a pharmaceutically acceptable salt, or a pharmaceutically acceptable polymorph, solvate, hydrate, dehydrate, co-crystal, anhydrous, or amorphous form thereof, in an amount of from about 0.05 mg to about 50 mg, preferably in an amount of from about 0.25 mg to about 10 mg, and more preferably in an amount of from about 0.5 mg to 5 mg.

In exemplary embodiments, the PG, a functional derivative thereof, a pharmaceutically acceptable salt, or a product thereof can be delivered in the form of liposomes, optionally mixed with one or more of the above additives. Although the compositions of the present disclosure may be delivered in any form, for treatment of skin disorders, topical dosage forms may be preferable.

Topical, Transdermal and Mucosal Dosage Forms

Topical dosage forms of the disclosure include, but are not limited to, creams, lotions, ointments, gels, shampoos, sprays, aerosols, solutions, emulsions, and other forms known to one of skill in the art. (e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985)). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art.(e.g., Remington's Pharmaceutical Sciences, $18^{th}$ Ed., Mack Publishing, Easton, Pa. (1990)).

Transdermal and mucosal dosage forms of the active composition include, but are not limited to, creams, lotions, ointments, gels, solutions, emulsions, suspensions, suppositories, ophthalmic solutions, patches, sprays, aerosols, or other forms known to one of skill in the art. {e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985)). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to water, phosphate-buffered saline, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of the active composition. For example, penetration enhancers can be used to assist in delivering the active ingredients to or across the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of an active composition can be used to further adjust the properties of the resulting composition.

EXAMPLES

Now having described the embodiments of the compositions and methods for modulating and/or normalizing keratinocyte function and/or proliferation, methods of modulating phosphatidylglycerol levels in keratinocytes, and methods and compositions for treating skin conditions in general, the following examples describe certain embodiments of compositions and methods for modulating and/or normalizing keratinocyte function and/or proliferation, methods of modulating phosphatidylglycerol levels in keratinocytes, and methods and compositions for treating skin conditions. While such embodiments are described in connection with Examples 1-3 and the corresponding text and figures, there is no intent to limit the embodiments of the present disclosure to these descriptions. On the contrary, the intent is to cover all alternatives, modifications, and equivalents included within the spirit and scope of embodiments of the present disclosure.

Example 1

This example provides evidence that long-term exposure of keratinocytes to elevated extracellular calcium concentration increases PLD activity and that elevated extracellular calcium, but not 1,25-dihydroxyvitamin D3, increases PLD-mediated phosphatidylglycerol production in cells labeled with [$^3$H] or [$^{14}$C]glycerol. This increase in phosphatidylglycerol production upon chronic elevated extracellular calcium exposure is not entirely the result of an increase in glycerol uptake. In addition, PMA increases PLD activity but does not enhance phosphatidylglycerol formation. Since (1) PLD-1, but not PLD-2, expression and activity is increased by 1,25-dihydroxyvitamin $D_3$ and (2) PMA activates PLD-1 to a greater extent than PLD-2, this suggests that radiolabeled PG production upon exposure to glycerol is a measure of PLD-2 activation in keratinocytes.

Experimental

Materials

Membranes obtained from Sf9 insect cells overexpressing PLD-2 were provided by Onyx Pharmaceuticals, California, U.S. [$^3$H] Oleic acid, [$^3$H] palmitoylphosphatidylcholine, [$^3$H] glycerol {three different forms were used as products were discontinued: [1,2,3-$^3$H]glycerol (specific activity of 200 mCi/mmol), [1,2,3-$^3$H] glycerol (specific activity of 40-80 mCi/mmol) and [2-$^3$H] glycerol (specific activity of 200 mCi/mmmol)} and [1,3-$^{14}$C]glycerol were obtained from NEN/DuPont (Boston, Mass., U.S.). Egg-derived phosphatidylglycerol, soy-derived phosphatidylglycerol, phosphatidylethanolamine, phosphatidylcholine and standards of phosphatidylethanol, phosphatidic acid and phosphatidylglycerol were purchased from Avanti Polar Lipids (Alabaster, Ala., U.S.). Phosphatidylinositol 4,5-bisphosphate was obtained from Calbiochem (San Diego, Calif., U.S.) or Sigma (St. Louis, Mo., U.S.). Calcium-free MEM and antibiotics were purchased from Biologos, Inc. (Maperville, Ill., U.S.). Bovine pituitary extract, epidermal growth factor and HEPES solution (1 M, pH 7.4) were obtained from Gibco BRL (Grand Island, N.Y., U.S.). ITS+ was supplied by Collaborative Biomedical Products (Bedford, Mass., U.S.) and dialyzed fetal bovine serum by Atlanta Biologicals (Atlanta, Ga., U.S.). Silica gel 60 TLC plates with concentrating zone were obtained from EM Science (Gibbstown, N.J., U.S.). AU other reagents were obtained from standard suppliers and were of the highest grade available.

In Vitro Assay of Phosphatidylglycerol Formation

PLD-2 activity was measured in vitro with [$^3$H-palmitoyl] phosphatidylcholine as substrate. Radiolabeled phosphatidylcholine was incorporated into lipid vesicles prepared from phosphatidylethanolamine, phosphatidylcholine and phosphatidylinositol 4,5-bisphosphate as described in R. D. Griner, F. Qin, E. M. Jung, C K. Sue-Ling, K. B. Crawford, R. Mann-Blakeney, R. J. Bollag, and W. B. Bollag, 1,25-Dihydroxyvitamin D$_3$ induces phospholipase D-1 expression in primary mouse epidermal keratinocytes, J. Biol. Chem. 274 (1999) 4663-4670, incorporated herein by reference. Glycerol and/or ethanol was combined with the liposomes and the reaction initiated by the addition of PLD-2-overexpressing Sf9 cell membranes, which were provided by Onyx Pharmaceuticals, Richmond, Calif., U.S. The reaction was then allowed to proceed at 37° C. for 30 minutes prior to termination by the addition of 0.2% SDS containing 5 mM EDTA. Lipids were extracted according to the method of Bligh and Dyer and radiolabeled phospholipids separated and quantified, as described in W. B. Bollag, "Measurement of phospholipase D activity, Methods" Mol. Biol. 105 (1998) 151-160, incorporated herein by reference.

Cell Culture

Primary epidermal keratinocytes were prepared from 1-3-day old neonatal ICR mice after trypsin flotation of the skin and mechanical separation of the epidermis from the dermis. The epidermal cells were released by scraping, collected by centrifugation and plated in 6-well dishes in a medium consisting of MEM containing 25 μM calcium, 2% dialyzed fetal bovine serum, 2 mM glutamine, 5 ng/mL EGF, ITS (6.25 μg/mL insulin+6.25 μg/mL transferrin+6.25 ng/mL selenious acid+5.35 μg/mL linoleic acid+1.25% bovine serum albumin), 100 U/mL penicillin, 100 μg/mL streptomycin and 0.25 μg/mL fungizone. After an overnight incubation, the cells were refed with serum-free keratinocyte medium (SFKM), in which 2% dialyzed fetal bovine serum was replaced with 90 μg/mL bovine pituitary extract. Cells were refed with fresh medium every 1-3 days.

PLD Activity and [$^3$HI or [$^{14}$C1Phosphatidylglycerol Formation

For the PLD assay cultured primary keratinocytes were labeled for 20-24 hours with 2.5 μCi/ml [$^3$H] oleic acid. The cells were then exposed to vehicle or 100 nM PMA in the presence of 0.5% ethanol for 30 minutes. To measure the formation of radiolabeled phosphatidylglycerol, cells were treated for 24 hours with SFKM containing vehicle, 250 nM 1,25-dihydroxyvitamin D$_3$ or 125 μM calcium and then labeled for an additional 30 minutes with 1-2.5 μCi/mL [$^3$H] or 0.4-0.5 μCi/mL [$^{14}$C]glycerol. For experiments investigating the extracellular calcium dependence of PG formation, cells were incubated for 24 hours in SFKM containing various calcium concentrations prior to the addition of 5 μCi/mL [$^3$H]glycerol for 30 minutes. In some cases, cells were stimulated with 25 μM calcium (control)—or 125 μM calcium-containing SFKM for 24 hours prior to the addition of [$^{14}$C] glycerol in the presence and absence of 1% ethanol. To measure phosphatidylglycerol formation in response to PMA, unlabeled cells were stimulated with 100 nM PMA in the presence of radiolabeled glycerol, as above. Reactions were terminated and the radiolabeled phosphatidylalcohol extracted, separated by thin-layer chromatography and quantified as described by Bollag (1998), referenced above.

Demonstration of Radiolabel in the Headgroup Position of [$^{14}$C]Phosphatidylglycerol Keratinocytes pretreated for 24 hours with control (25 μM calcium) or 125 μM calcium-containing medium were exposed to 0.4-0.5 μCi/mL [$^{14}$C]glycerol for an additional 30 minutes. Lipids were extracted into chloroform/methanol as described above. Dried lipid extracts were then solubilized in phospho lipase buffer (100 mM Tris, pH 7.4, 6 mM MgCl$_2$+ 0.1% Triton-X100) by extensive vortexing and a short incubation at 37° C. and approximately half of each extract was transferred into a clean tube. Distilled water (untreated) or 1 IU/mL (final concentration) of *Streptomyces chromofuscus* PLD (Sigma, St. Louis, Mo.) diluted in distilled water (PLD-treated) was then added to each of the lipid extract samples, which were incubated at 37° C. for 60 minutes. Released headgroups were then separated from phospholipids by extraction into the aqueous layer, essentially according to the method of Folch. J. Rolch, M. Lees, G. H. S. Stanley, "A simple method for the isolation and purification of total lipids from animal tissues", J. Biol. Chem. 226 (1957) 497-509, incorporated herein by reference. Briefly, 75 μL reaction mixtures were diluted with 1.5 mL of chloroform/methanol (2:1 volume:volume) followed by the addition of 300 μL of 0.05 M NaCl. A portion of the upper aqueous layer was then collected and quantified by liquid scintillation spectrometry. PLD-released radioactivity in the aqueous phase was calculated as the amount released in the PLD-treated sample minus the amount detected in the corresponding untreated sample. In other experiments, PG was first isolated from lipid extracts by thin-layer chromatography as described above and visualized with iodine vapor. PG was extracted from the thin-layer plate using chloroform/methanol (2:1 volume:volume) and dried under nitrogen. The isolated PG was then solubilized, incubated with and without bacterial PLD and extracted as above. Following removal of the aqueous aliquot for counting, the remaining aqueous phase was aspirated, and the organic phase dried under nitrogen. This lipid extract was then separated by thin-layer chromatography and PG and phosphatidic acid in the samples quantified as above.

[$^3$H]Glycerol Uptake

Confluent primary keratinocytes were incubated for 30, 60, 90, 120, 300 or 600 seconds with SFKM containing 20 mM HEPES (for additional pH buffering), 1 μCi/mL [$^3$H]glycerol and 0.1% DMSO (control) or 100 nM PMA. Reactions were terminated by washing three times with ice-cold phosphate-buffered saline lacking divalent cations. The cells were subsequently solubilized in 0.3 M NaOH and aliquots of this extract subjected to liquid scintillation counting. Counts obtained from duplicate samples at each time point were averaged and graphed, and a linear equation was determined for each condition. Correlation coefficients obtained were typically 0.99 or greater (mean correlation coefficient for control was 0.992±0.002 and for PMA, 0.994±0.001). Slopes obtained from multiple experiments were averaged and analyzed statistically for significant differences between conditions.

The linearity of glycerol uptake determined above allowed measurement of uptake at a single time point to determine the effects of other treatments on this process. Thus, confluent keratinocytes were preincubated for 30 minutes with 0.1% DMSO (control) or 100 nM PMA prior to measuring [$^3$H] glycerol uptake as above but at 5 minutes only. Similarly, near-confluent primary keratinocytes were incubated for 24 hours with SFKM containing various calcium concentrations prior to measurement of radiolabeled glycerol uptake for 5 minutes.

Statistical Analysis

The significance of differences between mean values was determined using analysis of variance (ANOVA), as performed by the program Instat (GraphPad Software, San Diego, Calif.).

Results

PLD-2 Utilizes Glycerol as a Primary Alcohol for the Transphosphatidylation Reaction in Vitro (Characterization of the Response)

Figure 5:
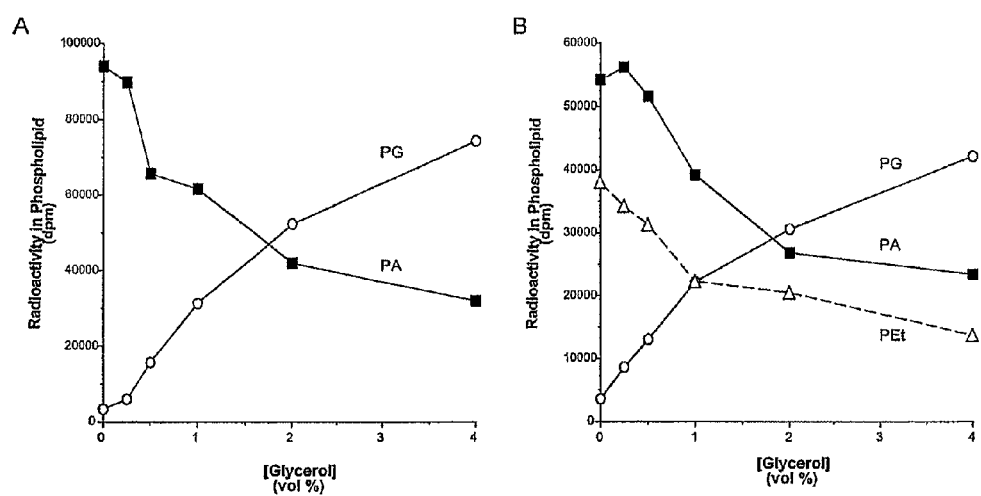
FIGS. 5A and B illustrate that glycerol serves as a substrate for phospholipase D in the transphosphatidylation reaction in vitro. Liposomes were prepared from [$^3$H-dipalmitoyl]phosphatidylcholine, phosphatidylethanolamine, phosphatidylcholine and phosphatidylinositol 4,5-bisphosphate by sonication. Glycerol at the indicated concentrations in the absence (A) or presence of 1% ethanol (B) was added to the reaction mix. Reactions were initiated by the addition of Sf9 PLD2-overexpressing membranes (1 µg protein), incubated for 30 minutes at 37° C. and terminated by the addition of 0.2% SDS (±5 mM EDTA). Lipids were extracted, separated, and quantified. The figure is representative of at least two additional experiments. There was some variability in the absolute levels of phosphatidic acid (PA), PG and phosphatidylethanol (PEt) formed, likely due to variations in the extent of formation of multilamellar vesicles during sonication.

In intact cells, PLD has the unique property of catalyzing not only the hydrolysis of phospholipids to form phosphatidic acid but also, in the presence of primary alcohols, a transphosphatidylation reaction that results in the production of phosphatidylalcohols. Thus, the generation of phosphatidylalcohols has been used as a measure of PLD activity. Typically, primary alcohols such as ethanol or 1-butanol are used since this results in the production of novel phosphatidylalchohols that are not readily metabolized by the cell. Previous studies in intact cells have suggested that the physiological primary alcohol, glycerol, can also serve as a substrate for the transphosphatidylation reaction. PLD2-overexpressing Sf9 membranes, were used to investigate whether glycerol is a substrate for PLD2 in vitro. As shown in FIG. 5 A, PLD2 catalyzed the formation of PG from phosphatidylcholine in the presence of glycerol. This formation was dependent on the concentration of glycerol in the reaction mix (FIG. 5A), as well as the amount of PLD2 added and the time of incubation (data not shown). Furthermore, glycerol could compete with the primary alcohol ethanol to generate PG in place of phosphatidylethanol (FIG. 5B). PLD-1 was also observed to generate PG in vitro in the presence of glycerol (data not shown).

Figure 6:
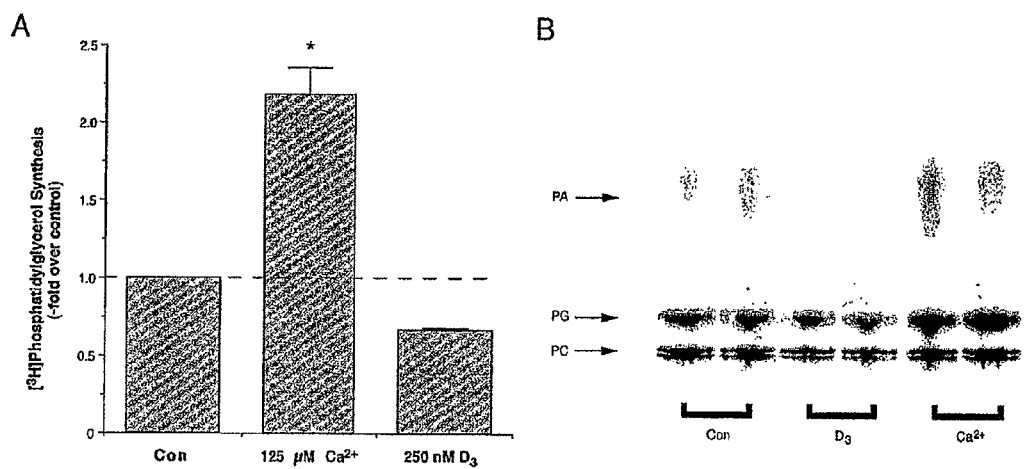
FIG. 6 demonstrates that phosphatidylglycerol formation is increased in differentiating cells exposed to elevated extracellular calcium concentrations but not 1,25-dihydroxyvitamin $D_3$. Near-confluent keratinocytes were incubated with (A) 25 µM-calcium-SFKM containing vehicle (Con; 0.05% ethanol), 250 nM 1,25-dihydroxyvitamin $D_3$ ($D_3$), or 125 µM calcium (+0.05% ethanol; $Ca^{2+}$) for 24 hours. 2.5-5 µCi/well [$^3$H]glycerol were then added for an additional 30 minutes at 37° C. Reactions were terminated by the addition of 0.2% SDS (+5 mM EDTA) and phospholipids extracted, separated, and quantified. Results are expressed as -fold over the control value and represent the means±SEM of 3 separate experiments; *$p<0.001$ versus the control. The thin-layer chromatogram shown in Panel B is representative of the three experiments quantified in Panel A.

The Production of Radiolabeled Phosphatidyl Glycerol, Formed Upon Addition of [$^3$H] or [$^{14}$C]Glycerol to Intact Cells, is Increased Upon Exposure of Keratinocytes to an Elevated Calcium Concentration and Decreased with 1,25-Dihydroxyvitamin D$_3$ Treatment The inventors have shown previously that the keratinocyte-differentiating agent, 1,25-dihydroxyvitamin D$_3$ increases PLD-1 expression and activity after a 24-hour exposure (see Griner, et al. referenced above). The current example investigated the effect of 1,25-dihydroxyvitamin D$_3$ and another agent that triggers keratinocyte differentiation, elevated extracellular calcium levels, on phosphatidylglycerol formation in cells pretreated for 24 hours prior to addition of [$^3$H] glycerol. Based on the previous results, it was anticipated that 1,25-dihydroxyvitamin D$_3$ would increase the generation of PG, since this agent stimulated PLD-1 activity and expression. Unexpectedly, exposure to 1,25-dihydroxyvitamin D$_3$ did not increase radiolabeled PG formation relative to control cells, and in fact, there was instead an apparent decrease observed (FIG. 6). On the other hand, pretreatment with 125 µM calcium-containing medium induced an increase in the subsequent production of PG (FIGS. 6A and B). This result suggested a possible elevated calcium-induced activation of PLD, or the possibility that other pathways, such as a mechanism in which glycerol-3-phosphate is added to CDP-diacylglycerol, might be involved in PG synthesis.

The Effect of Elevated Calcium Concentrations on PG Production, and Glycerol Uptake, is Dose-Dependent Elevated extracellular calcium levels induce various stages of keratinocyte differentiation in a concentration-dependent manner. Calcium concentrations in the range of 100-125 µM stimulate the expression of keratin-1, a marker of early (spinous) differentiation, whereas higher concentrations induce markers of later differentiation, e.g., transglutaminase activity. Thus, the dose-dependence of the effect of elevated extracellular calcium levels on PG production was investigated herein. PG formation in response to elevated extracellular calcium concentrations [over the range 25 µM (control) to 1 mM] exhibited a biphasic dose dependence (FIG. 7A). Thus, maximal stimulation of radiolabeled PG formation was observed at 125 µM calcium, with a gradually declining effect at higher calcium concentrations.

The ability of intermediate calcium concentrations to stimulate PG formation maximally could be the result of an increase in glycerol uptake, an enhancement of PLD activity or both. The effect of pretreatment of keratinocytes with various calcium concentrations on subsequent radiolabeled glycerol uptake was determined as described. Pre-exposure to 125 µM and 250 µM calcium-containing medium induced an increase (of 56% and 41%, respectively) in glycerol uptake relative to the 25 µM calcium control, whereas glycerol uptake in 500 µM-calcium-pretreated keratinocytes was approximately equivalent to the control value (FIG. 7B). On the other hand, a concentration of 1 mM induced a slight but not significant inhibition (in these experiments) of glycerol uptake. The small increase in glycerol uptake observed with 125 µM calcium pretreatment is unlikely by itself to account for the large increase in radiolabeled PG production, suggesting that PLD was also activated by the intermediate calcium concentrations.

Figure 8:
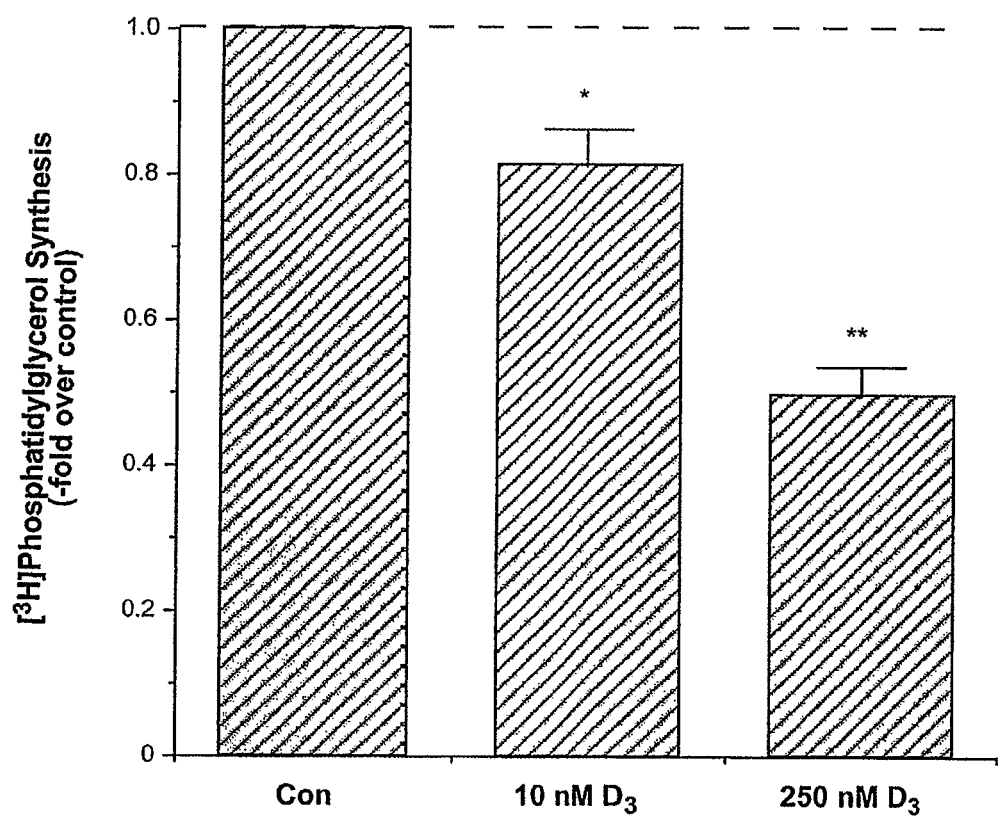
FIG. 8 is a bar graph showing that phosphatidylglycerol formation is inhibited in differentiating cells exposed to intermediate and high concentrations of 1,25-dihydroxyvitamin $D_3$. Near-confluent keratinocytes were incubated with SFKM containing 0.05% ethanol (Con), 10 nM 1,25-dihydroxyvitamin $D_3$, or 250 nM 1,25-dihydroxyvitamin $D_3$ ($D_3$) for 24 hours. 2.5-5 µCi/well [$^3$H]glycerol were then added for an additional 30 minutes at 37° C. Reactions were terminated by the addition of 0.2% SDS (+5 mM EDTA) and phospholipids extracted, separated, quantified as described in Methods and expressed as -fold over the control value. Results represent the means±SEM of 3 separate experiments; *$p<0.01$, **$p<0.001$ versus the control.

The ability of intermediate calcium concentrations to stimulate PG synthesis suggested that this process was associated with early differentiation events. Therefore, the effect of an intermediate 1,25-dihydroxyvitamin D$_3$ concentration on PG synthesis was examined, which is also known to stimulate expression of the early differentiation marker keratin-1 (10 nM). In contrast to the results with the intermediate calcium concentrations, a concentration of 1,25-dihydroxyvitamin D$_3$ did not increase PG synthesis, and in fact, both the intermediate and high (250 nM) concentrations of 1,25-dihydroxyvitamin D$_3$ significantly inhibited PG production (FIG. 8).

Increased Radiolabeled Phosphatidylglycerol Formation Upon Treatment with an Elevated Calcium Concentration in Intact Cells is Mediated, at Least in Part, by PLD As observed in FIG. 6B, elevated extracellular calcium concentration appeared to induce an increase not only in the synthesis of PG but also of phosphatidylcholine and phosphatidic acid. Therefore, it was possible that calcium enhanced general phospholipid synthesis, stimulating glycerol incorporation into the phospholipid backbone rather than the headgroup, and that therefore increased PG synthesis occurred independently of PLD activity. Since ethanol and glycerol both act as a substrate for the transphosphatidylation reaction (FIG. 5B), ethanol was used to determine whether elevated extracellular calcium concentration-elicited stimulation of PG formation occurred through the activation of PLD. Ethanol (1%) was added to keratinocytes pretreated with 125 µM calcium minutes before initiation of PG production with

Figure 9:
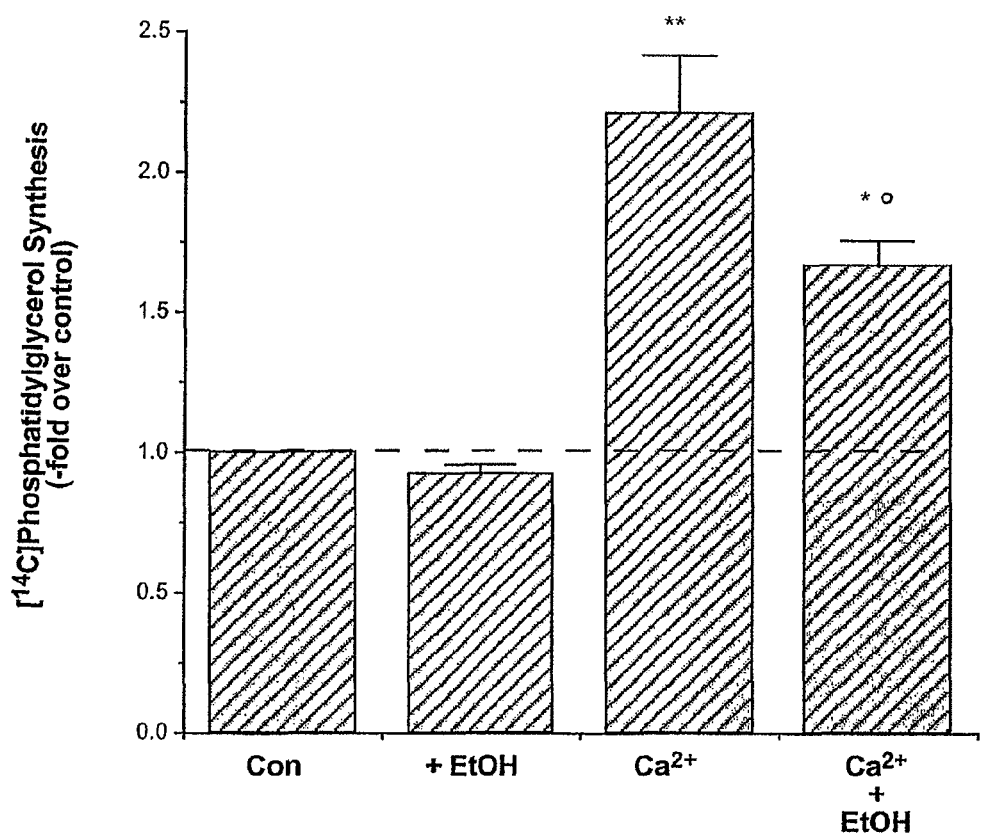
FIG. 9 is a bar graph illustrating that the extracellular calcium concentration-stimulated phosphatidylglycerol formation is inhibited by ethanol. Near-confluent keratinocytes were incubated with 25 µM-calcium SFKM (control) or 125 µM-calcium SFKM for 24 hours. The cells were then incubated for an additional 30 minutes with 0.5-1 µCi/well [$^{14}$C] glycerol in the presence and absence of 1% ethanol. Reactions were terminated by the addition of 0.2% SDS 5 mM EDTA), and radiolabeled PG was extracted, separated by thin-layer chromatography and quantified. Values are expressed as -fold over the control (without ethanol) and represent the means±SEM of 4 separate experiments; *$p<0.01$, **$p<0.001$ versus the control value, °$p<0.01$ versus 125 µM calcium-SFKM alone.

[$^{14}$C]glycerol. As shown in FIG. 9, ethanol significantly inhibited PG formation stimulated by preexposure to elevated extracellular calcium levels, without affecting basal (control) PG production. The ability of ethanol to compete with glycerol suggests that some, if not all, elevated calcium-stimulated PG formation is the result of an enhancement of PLD activity.

The involvement of PLD in elevated extracellular calcium-induced PG synthesis was further demonstrated by the ability of bacterial PLD to release radiolabel from lipid extracts and isolated PG. In these experiments, cells were pretreated with or without 125 µM calcium-containing medium for 24 hours prior to addition of [$^{14}$C]glycerol for 30 minutes. Lipid extracts were then prepared, solubilized in a Triton X100-containing buffer, and incubated with or without bacterial PLD for 1 hour. This bacterial PLD has been used to quantify phosphatidylglycerol in amniotic fluid, through its ability to release the glycerol headgroup. Released headgroups were then partitioned into the aqueous phase using the Folch method, as described above. Upon incubation with bacterial PLD, [$^{14}$C]glycerol-labeled lipid extracts from 125 µM calcium-pretreated cells released approximately four times the amount of radiolabel into the aqueous fraction as those from control-pretreated cells (control: 1.00±0.09; calcium: 4.2±0.4-fold over the control level; p<0.001 with values representing the means±SEM of 6 samples from 3 separate experiments). This result suggests that more glycerol was being incorporated into the headgroup position with calcium exposure, consistent with enhancement of a PLD-mediated transphosphatidylation reaction.

Figure 10:
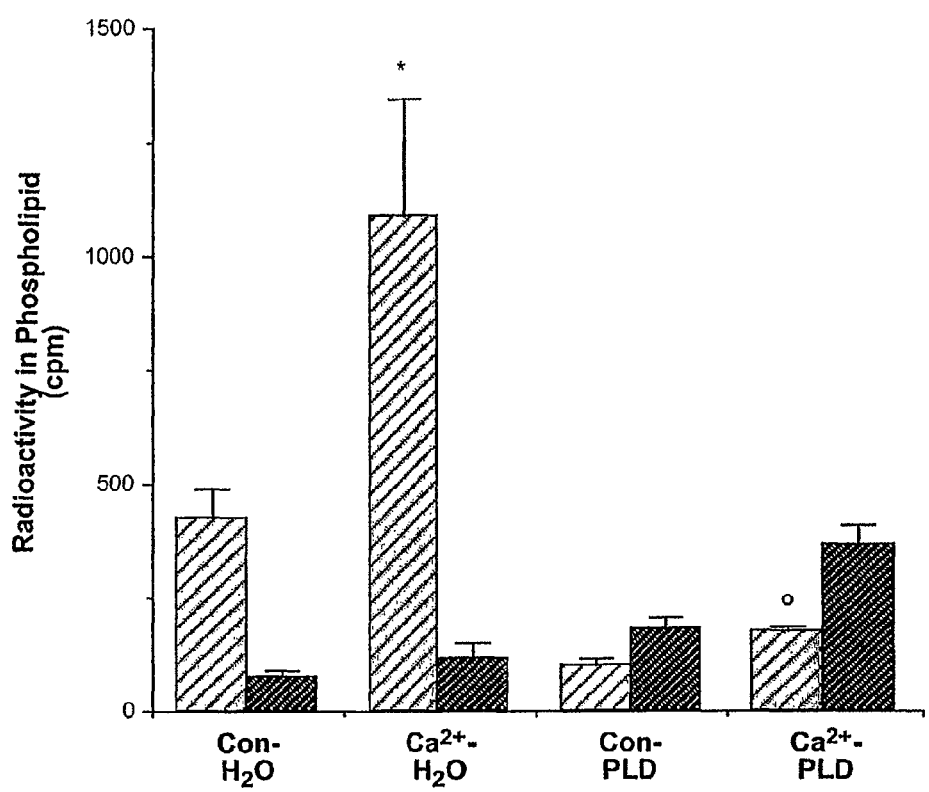
FIG. 10 shows that increased radiolabel was released by bacterial phospholipase D from phosphatidylglycerol isolated from elevated extracellular calcium-pretreated versus control cells. Near-confluent keratinocytes were incubated with 25 µM-calcium SFKM (control) or 125 µM-calcium SFKM for 24 hours. The cells were then incubated for an additional 30 minutes with 1 µCi/well [$^{14}$C]glycerol, followed by extraction of the lipids into chloroform/methanol and separation of PG by thin-layer chromatography. After solubilization, PG isolated from control (Con) or 125 μM calcium-treated (Ca$^{2+}$) cells was incubated with (PLD) or without (H$_2$O) bacterial PLD, and the radioactivity remaining in PG (light striped bars) and phosphatidic acid (dark striped bars) was quantified after thin-layer chromatographic separation. Values represent the means±SEM from three experiments; *p<0.001 versus the corresponding untreated control value, °p<0.001 versus the corresponding untreated calcium-treated value.

Similar experiments using PG isolated from control or elevated extracellular calcium-pretreated cells are shown in FIG. 10. Again, bacterial PLD released greater than 3-fold more radioactivity from PG isolated from 125 µM calcium-pretreated cells than from control cells (control: 1.00±0.04; calcium: 3.3±0.5-fold over the control level; p<0.01 with values representing the means±SEM of 6 samples from 3 separate experiments). Thin-layer chromatographic analysis of the bacterial PLD-treated and -untreated PG samples demonstrated that a portion of the radiolabeled PG was converted to radiolabeled PA, indicating that some of the glycerol was present in the phospholipid backbone (FIG. 10). However, only approximately 40% of the original radiolabel found in PG was recovered in PA, indicating that approximately 60% of the radiolabel in PG was present in the headgroup position.

Figure 11:
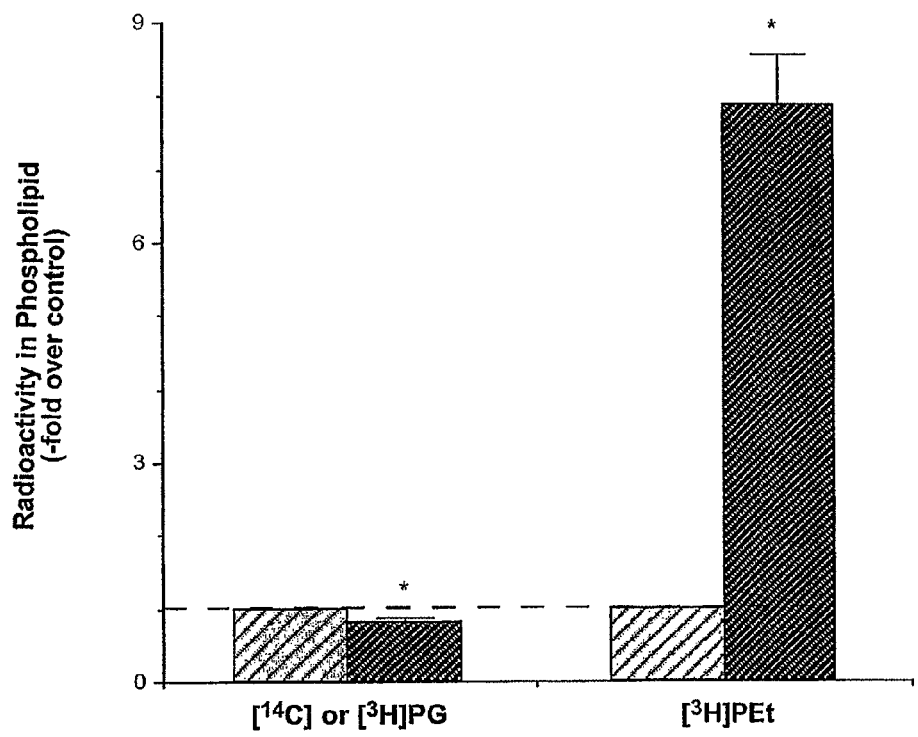
FIG. 11 is a bar graph showing that Phorbol 12-myristate 13-acetate (PMA) does not induce phosphatidylglycerol formation despite activating PLD. Near-confluent keratinocytes were incubated without radiolabel (for phosphatidylglycerol production) or pre-labeled with 2.5 μCi/mL [$^3$H]oleate (for phosphatidylethanol formation) for 20-24 hours. The cells were then stimulated for 30 minutes with vehicle (0.05-0.1% DMSO; Con) or 100 nM PMA in the presence of [$^3$H]glycerol (for phosphatidylglycerol production), or in the presence of 0.5% ethanol (for phosphatidylethanol formation). Reactions were terminated by the addition of 0.2% SDS (±5 mM EDTA) and radiolabeled phosphatidylglycerol (PG), or phosphatidylethanol (PEt) was extracted, separated by thin-layer chromatography and quantified. Values are expressed as -fold over control and represent the means±SEM of three separate experiments performed in duplicate or triplicate; *p<0.02 versus the appropriate control by an unpaired Student's t-test.
Figure 12:
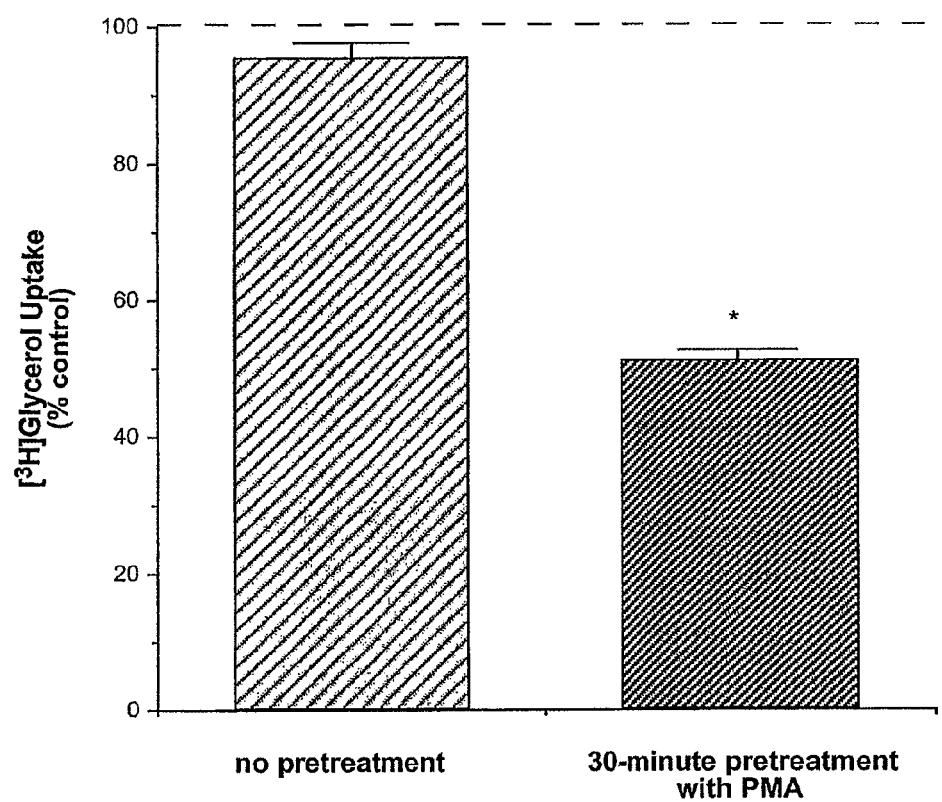
FIG. 12 illustrates that pretreatment, but not simultaneous incubation, with PMA inhibits [$^3$H]glycerol uptake. Glycerol uptake was measured in cells pretreated or treated simultaneously with and without PMA. For the "no pretreatment" samples, cells were incubated for 5 minutes in SFKM containing 20 mM HEPES, 1 μCi/mL [$^3$H]glycerol and 0.1% DMSO (control) or 100 nM PMA. For the "30-minute pretreatment with PMA" samples, confluent keratinocytes were pre-incubated for 30 minutes in SFKM containing 0.1% DMSO (control) or 100 nM PMA. Cells were then incubated for 5 minutes in SFKM containing 20 mM HEPES and 1 μCi/mL [$^3$H]glycerol. For both sets of samples, radiolabeled glycerol uptake was measured. Values are the means of 3 (no pretreatment) or 5 (30-minute pretreatment) separate experiments performed in duplicate or triplicate; *p<0.001 versus the control value of 100% (dotted line).

Phorbol Ester Increases PLD Activity but does not Increase Radiolabeled PG Formation Another agent known to induce both sustained PLD activity in intact cells and keratinocyte differentiation is the phorbol ester, PMA. Therefore, the effect of PMA on PG formation was determined. PMA actually elicited a significant (p<0.01 by unpaired Student's t-test) decrease in PG production (FIG. 11, right), despite the fact that it simulated a large increase in PLD activity (p<0.02), monitored using the formation of radiolabeled phosphatidylethanol in [$^{3}$H]oleate-prelabeled as a measure (FIG. 11, left). The ability of PMA to inhibit radiolabeled PG production could be the result of a PMA-mediated decrease in glycerol uptake. Simultaneous incubation of keratinocytes with [$^{3}$H]glycerol in the presence and absence of 100 nM PMA elicited no significant effect on glycerol uptake measured over 10 minutes (FIG. 11, and slope values of PMA 0.998-±0.009-fold over the control value of 1.00, determined as described in Methods and in reference [25]; n=3). However, pretreatment of keratinocytes for 30 minutes with vehicle or PMA prior to addition of radiolabeled glycerol for 5 minutes resulted in a PMA-induced decrease in glycerol uptake (FIG. 12), suggesting an effect of phorbol ester on glycerol transport that needs time (greater than 10 minutes) to develop. These results, together with the inability of 1,25-dihydroxyvitamin $D_3$ to increase PG formation, suggest that the production of PG is not a universal corollary of PLD activation.

Discussion

An interesting and useful finding has been made with respect to PLD: its ability to utilize primary alcohols for the production of novel phosphatidylalcohols in a transphosphatidylation reaction. This characteristic has been exploited by signal transduction researchers to measure PLD activity specifically and to inhibit PLD-mediated signal generation. However, the current data demonstrates that there is a physiological alcohol, glycerol, for which PLD retains this ability to use unphysiological alcohols. Indeed, in in vitro experiments PLD2 demonstrates the capacity to utilize glycerol as a substrate for the transphosphatidylation reaction (FIG. 5). The results further demonstrate that by utilizing glycerol for the transphosphatidylation reaction, PLD generates a potential lipid signaling molecule, PG.

Figure 7:
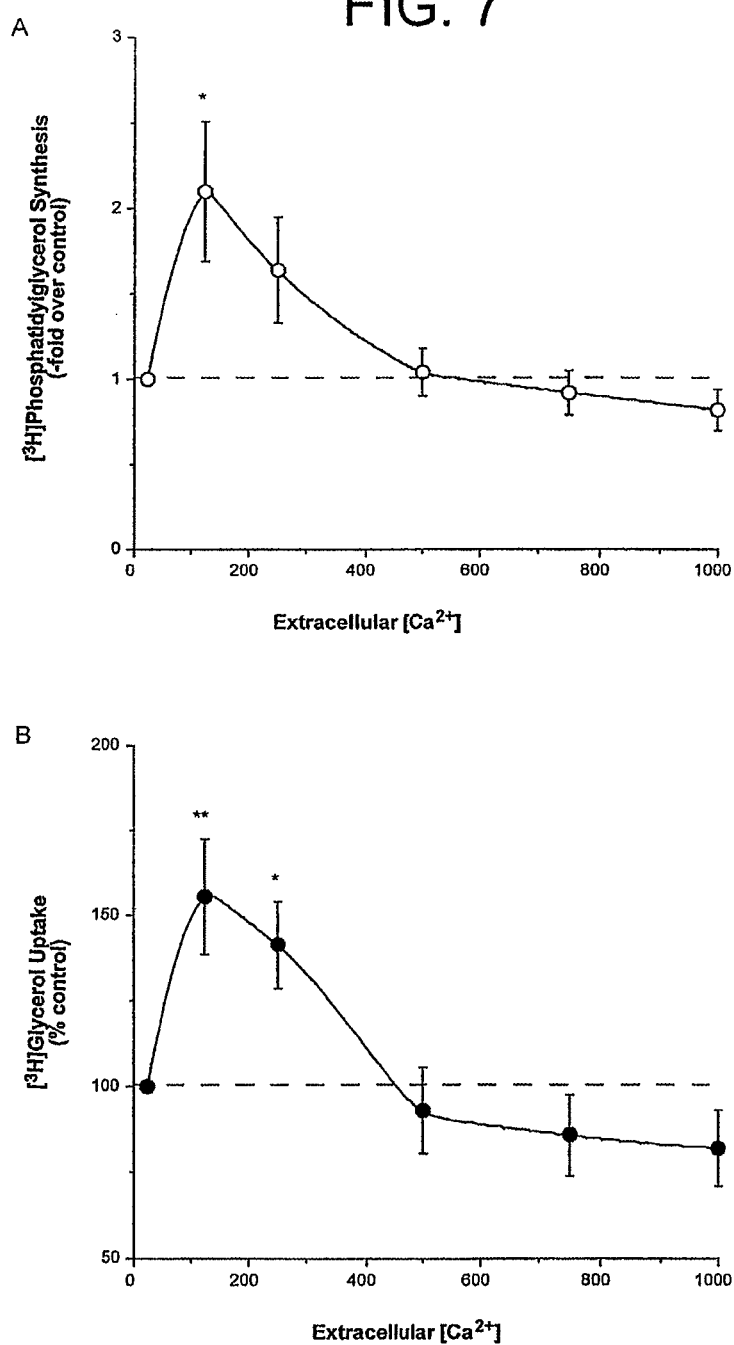
FIGS. 7A and B show that elevated extracellular calcium concentration increases phosphatidylglycerol production, and to a lesser extent glycerol uptake, in a dose-dependent manner. Near-confluent keratinocytes were incubated with SFKM containing various concentrations of calcium for 24 hours. (A) The cells were then incubated for an additional 30 minutes with 5 µCi/well [$^3$H]glycerol prior to termination of reactions with 0.2% SDS (±5 mM EDTA) and extraction, separation, and quantification of radiolabeled PG. Values are expressed as -fold over the control (25 µM-calcium-SFKM) and represent the means±SEM of 5 separate experiments; *$p<0.05$ versus the control value. (B) After a 24-hour pre-treatment with various calcium concentrations, the cells were incubated for 5 minutes with 1 µCi/well [$^3$H]glycerol in SFKM containing 20 mM HEPES, prior to termination of reactions by extensive washing with ice-cold phosphate-buffered saline lacking divalent cations. Values are expressed as -fold over the control (25 µM-calcium-SFKM) and represent the means±SEM of 5 separate experiments; **$p<0.01$, *$p<0.05$ versus the control value.

One of the corollaries of the mechanism of PLD-2 utilizes glycerol as a primary physiological alcohol for the transphosphatidylation reaction is the colocalization of PLD-2 and the glycerol uptake mechanism. Indeed, in previous work, the inventors of the present disclosure found that PLD2 was collocated with aquaporin-3 in caveolin-rich membrane microdomains (See Zhang and Bollag (2003) referenced above). Aquaporin-3 protein expression has been shown to localize to the basal layer of the epidermis. Consistent with this result, studies demonstrated decreased aquaporin-3 mRNA and protein expression, upon stimulation of primary keratinocytes with the differentiating agents, elevated extracellular calcium concentration and 1,25-dihydroxyvitamin $D_3$. The reduced expression also resulted in inhibited function, in that radiolabeled glycerol uptake was decreased by both elevated extracellular calcium concentration and 1,25-dihydroxyvitamin $D_3$. However, there was no significant difference in the inhibition by these two agents, suggesting that their disparate effect on radiolabeled PG production is not due to differences in their ability to inhibit uptake of the radiolabeled glycerol. On the other hand, the ability of 125 µM calcium to trigger a maximal increase in PG production is likely the result of its stimulation of PLD activity as well as its lack of inhibition of glycerol uptake (indeed, pretreatment with this concentration of calcium stimulated glycerol uptake). Inhibition of glycerol uptake by higher calcium concentrations probably explains the biphasic PG production observed in response to various calcium concentrations (FIG. 7). Interestingly, PMA also inhibited glycerol uptake (FIG. 12), consistent with the idea that PKC modulates aquaporin-3 function, as has been observed for aquaporin-4. High calcium concentrations are also reported to stimulate PKC activity, and this might represent the mechanism by which elevated calcium levels affect glycerol uptake.

The ability of elevated extracellular calcium concentrations to stimulate PG production, whereas the additional keratinocyte differentiating agents, 1,25-dihydroxyvitamin $D_3$ and PMA did not, suggests an important difference in the mechanism by which these three agents trigger the differentiative response. Thus, maximal elevated extracellular calcium and 1,25-dihydroxyvitamin $D_3$ concentrations act synergistically to increase various markers of keratinocyte differentiation, rather than less than additively as would be expected if the two agents utilized a completely common pathway. In addition, PMA is known to produce changes in keratinocytes consistent with induction of late (granular) differentiation and actually inhibits markers of early differentiation, in contrast to the effects of elevated extracellular calcium and 1,25-dihydroxyvitamin $D_3$ levels. PLD-1 has been proposed to mediate at least in part, 1,25-dihydroxyvitamin $D_3$-induced keratinocyte late differentiation, based on the findings that exogenous (bacterial) PLD can induce keratinocyte differentiation and 1,25-dihydroxyvitamin $D_3$ increases PLD-1 expression and activity. On the other hand, 1,25-dihydroxyvitamin $D_3$ does not enhance PG formation (FIGS. 6 and 8), nor does PMA (FIG. 11). Since 1,25-dihydroxyvitamin $D_3$ does not increase PLD-2 expression and PMA is reported to activate PLD-1 to a greater extent than PLD-2, in keratinocytes radiolabeled PG production upon exposure to glycerol may be a measure of PLD-2 activation. Thus, this assay provides a way to monitor the activity of a single PLD, PLD-2, in an intact cell system possessing both PLD isoforms.

An interesting aspect of these studies was the observed formation of phosphatidylcholine and phosphatidic acid upon addition of radiolabeled glycerol. In PG, the glycerol is presumably incorporated, at least in part, as the headgroup in a transphosphatidylation reaction, since the incorporation can be inhibited by ethanol (FIG. 9). Indeed, in vitro experiments utilizing bacterial PLD to release phospholipid headgroups, demonstrated that elevated extracellular calcium pretreatment enhanced the incorporation of glycerol into the headgroup position (FIG. 10). In phosphatidylcholine and phosphatidic acid, the glycerol is most likely incorporated into the phospholipid as a glycerol backbone. Phosphatidic acid is formed de novo by the addition of two fatty acids (via fatty-acyl CoAs) to glycerol 3-phosphate, produced by the action of glycerol kinase on glycerol; the subsequent addition of choline (via CDP-choline) to dephosphorylated phosphatidic acid (diacylglycerol) produces phosphatidylcholine. Since radiolabeled glycerol was added for a total of 30 minutes only, this result would suggest rapid and active phospholipid synthesis. This idea is consistent with the role of keratinocytes in generating the lipids for forming the water permeability barrier of skin. It was also shown that radiolabeled glycerol is incorporated into the backbone of PG as well, accounting partially for the increase in radiolabeled PG formation. Thus, the present results confirm that PG synthesis can occur in at least two ways: through a PLD-mediated transphosphatidylation reaction and via the more traditional route of the addition of glycerol-3-phosphate to CDP-diacylglcyerol and subsequent removal of the phosphate group.

Several possibilities exist for the role of PG in keratinocytes. Based on the localization of glycerol-transporting aquaporin-3 to the basal layer in skin, one might expect this signaling pathway to function in a proliferative capacity or perhaps in early differentiation events. This idea is consistent with the observation that radiolabeled PG production is stimulated maximally by an intermediate calcium concentration (125 µM; FIG. 7) known to induce near-maximal expression of keratin-1, a marker of early differentiation. Such an interpretation would also be supported by the data indicating a role for PG in PKC-βII-mediated mitotic progression. While a previous study has reported no detectable expression of PKC-β by northern analysis of mouse keratinocytes, other studies in both mouse and human have suggested expression of this isoform in keratinocytes. On the other hand, recent generation and initial characterization of an aquaporin-3 null mouse mutant indicates the importance of this aquaglyceroporin to normal skin physiology. These null mice display a skin phenotype of dry skin and altered water-holding capacity. In addition, absorption of the water through epidermis stripped of its water-impermeable outer layer (the stratum corneum) is abnormal in the aquaporin-3-null mice, suggesting a change in some aspect of the epidermal structure that inhibits its hydrating ability. Based on the present results, it is believed that the decreased formation of PG in aquaporin-3 null mice results in defects in keratinocyte growth and/or differentiation that result in the abnormal skin physiology observed in these mutants.

Example 2

This example provides additional evidence for a PLD2/AQP3/glyceol/PG module in keratinocytes, demonstrating that glycerol entering through an acid-sensitive aquaglyceroporin is utilized by PLD to form PG. In transient co-transfection studies AQP3 was co-expressed with reporter constructs in which promoters for markers of keratinocyte proliferative or differentiative status drive luciferase expression. These studies indicated that AQP3 co-expression inhibited the promoter activity of keratin 5, a marker of basal, proliferative keratinocytes, increased the promoter activity of keratin 10, a marker of early keratinocyte differentiation, and enhanced the effect of an elevated extracellular calcium level on the promoter activity of involucrin, a marker of intermediate differentiation. Glycerol and 1,2-propylene glycol (glycerol missing one hydroxyl group on the number 3 terminal carbon) inhibited DNA synthesis in a dose-dependent manner both in a low (25 µM) and an intermediate (125 µM) calcium concentration, whereas equivalent concentrations of the osmotically active agents, xylitol and sorbitol, had little or no effect. Direct provision of PG liposomes also inhibited DNA synthesis in a dose-dependent fashion in rapidly dividing keratinocytes, although in growth-inhibited cells PG liposomes dose dependently enhanced [$^3$H]thymidine incorporation into DNA. A trend for stimulation of transglutaminase activity by PG liposomes was also observed. These data support the idea of a signaling module consisting of AQP3, PLD2, glycerol, and PG and involved in promoting growth inhibition and/or early differentiation of proliferating keratinocytes.

Experimental Procedures

Keratinocyte Preparation and Cell Culture

Keratinocytes were prepared from ICR CD-I outbred mice in accordance with a protocol approved by the Institutional Animal Care and Use Committee. Briefly, the skins were harvested and incubated overnight in 0.25% trypsin at 4° C. The epidermis and dermis were separated and basal keratinocytes scraped from the underside of the epidermis. The cells were collected by centrifugation and incubated overnight in an atmosphere of 95% air/5% carbon dioxide at 37° C. in plating medium as described in Dodd M E, Ristich V L, Ray S, Lober R M, Bollag W B (2005) Regulation of protein kinase D during differentiation and proliferation of primary mouse keratinocytes. J Invest Dermatol 125:294-306, incorporated herein by reference. The plating medium was replaced with serum-free keratinocyte medium (SFKM) also as in Dodd, et al., and the cells were refed every 1-2 days with fresh medium until use.

[$^3$H]Glycerol Uptake Assay

Near-confluent keratinocyte cultures were incubated for 24 hours in SFKM (25 µM calcium) or SFKM containing 125 µM calcium (125 µM $Ca^{2+}$-SFKM) and the glycerol uptake assay performed as previously described in Zheng & Bollag (2003). Briefly, cells were incubated with SFKM containing 20 mM HEPES (for additional pH buffering) and 1 µCi/mL [$^3$H] glycerol for 5 minutes, since it has previously been shown that this time point is in the linear range of [$^3$H] glycerol uptake (Zheng & Bollag (2003). Reactions were terminated by rapidly washing three times with ice-cold phosphate-buffered saline lacking divalent cations (PBS-). Cells were then solubilized in 0.3 M NaOH and [$^3$H]glycerol uptake quantified by liquid scintillation spectroscopy.

PG Synthesis

After incubation of near-confluent keratinocytes for 24 hours in SFKM (25 μM calcium) or SFKM containing 125 μM calcium (125 μM Ca$^{2+}$-SFKM), 0.5-1 μCi/mL [$^{14}$C] glycerol was added for 10 minutes and PG synthesis. Briefly, radiolabeled PG was extracted into chloroform/methanol and separated by thin-layer chromatography on silica gel 60 plates as described in Zheng, X., Ray, S, and Bollag, W. B. (2003) Biochim. Biophys. Acta, 1643, 25-36, incorporated herein by reference.

Co-Transfection Analysis

Co-transfection experiments were performed as described by Dodd, et al., using 1 ng of the pcDNA3 empty vector or a construct possessing AQP3, 1 ng of one of the reporter constructs in which the promoters for keratin 5, keratin 10 or involucrin drive expression of luciferase and 0.25 ng of the pRL-SV40 control vector (included in the Promega Dual Luciferase Reporter Assay kit) to normalize for transfection efficiency. The keratin 5 and keratin 10 promoter-luciferase constructs were provided by of Dr. Bogi Andersen (University of California, Irvine, Calif.); the involucrin promoter-luciferase construct was provided by Dr. Daniel Bikle (University of California, San Francisco, Calif.). Sub-confluent (approximately 30%) keratinocytes were transfected using TransIT-Keratinocyte according to the manufacturer's instructions. After 24 hours cells were refed with medium containing 25 μM (control) or 1 mM-Ca$^{2+}$ for an additional 24 hours. Luciferase activity was then measured using the Dual Luciferase Reporter Assay kit (Promega, Madison, Wis.) as directed by the manufacturer.

Assay of DNA Synthesis

[$^3$H]Thymidine incorporation into DNA was determined as a measure of DNA synthesis as previously described by Griner, et al., above. Near-confluent keratinocyte cultures were incubated for 24 hours in SFKM containing the indicated additions. PG was added in the form of liposomes prepared by bath sonication of dried PG in SFKM to make a stock solution of 2 mg/mL. [$^3$H]Thymidine at a final concentration of 1 μCi/mL was then added to the cells for an additional 1-hour incubation. Reactions were terminated by washing with PBS- and macromolecules precipitated with ice-cold 5% trichloroacetic acid. Cells were solubilized in 0.3 M NaOH and the radioactivity incorporated into DNA quantified by liquid scintillation spectroscopy.

Transglutaminase Assay

Keratinocytes were treated with PG liposomes, collected by scraping and centrifugation in homogenization buffer and lysed by sonication after one freeze-thaw cycle. Transglutaminase activity was monitored in the broken cells as the amount of [$^3$H]putrescine cross-linked to dimethylated casein as described in Bollag, W. B., Zhong, X., Dodd, M. E., Hardy, D. M., Zheng, X. and Allred, W. T. (2005) J. Pharm. Exp. Ther., 312, 1223-1231, incorporated herein by reference. The cross-linked putrescine-casein was precipitated with tricholoroacetic acid and collected by filtration. Data were normalized to the quantity of protein in each sample, determined using the Biorad protein assay with bovine serum albumin as standard, and expressed relative to the appropriate control.

Statistics

Experiments were performed a minimum of three times as indicated. Values were analyzed for statistical significance by analysis of variance (ANOVA) with a Student-Newmann-Keuls post-hoc test using Instat (GraphPad Software, San Diego, Calif.).

Results

Inhibition of Glycerol Uptake with Acidic Medium Inhibits PG Synthesis

Figure 13:
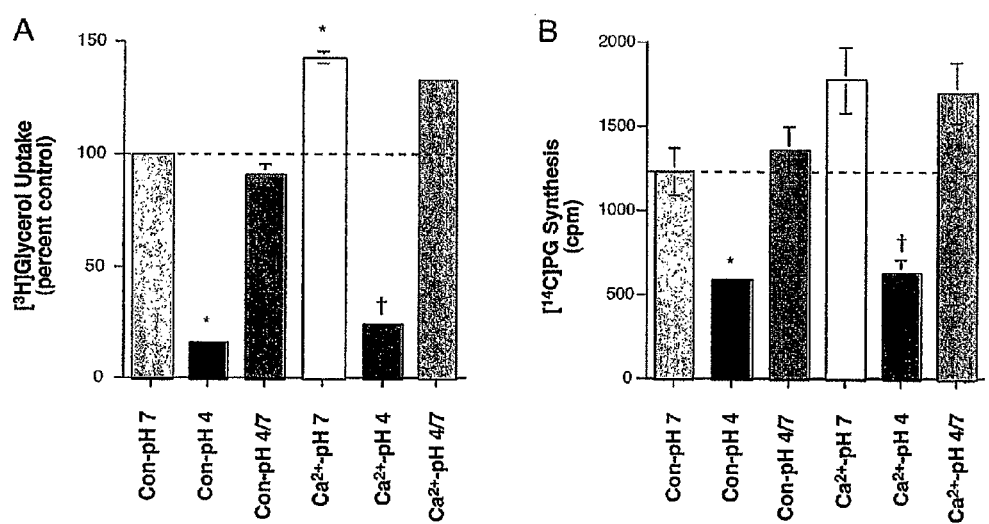
FIGS. 13A and B illustrate that an extracellular medium of pH 4 inhibits radiolabeled glycerol uptake (A) and PG synthesis (B). Keratinocytes were pretreated for 24 hours with control (25 μM Ca$^{2+}$) medium (Con) or 125 μM Ca$^{2+}$ (Ca$^{2+}$)-containing medium. Some cells were then incubated for 5 (panel A) minutes with medium of pH 4 prior to (A) measurement of [$^3$H] glycerol uptake for 5 minutes, or (B) [$^{14}$C]PG synthesis for 10 minutes, at pH 4 or 7 (7.4) as indicated. Results represent the means±SEM of (A) four or (B) three experiments performed in duplicate; *p<0.05, **p<0.001 versus the control value (glycerol uptake or PG synthesis in control cells measured at pH 7); †p<0.01, ††p<0.001 versus the Ca$^{2+}$ value measured at pH 7 (7.4). Note that the effects of low pH on [$^3$H]glycerol uptake (panel A) and [$^{14}$C]PG synthesis (panel B) were essentially reversible (compare pH 7 to pH 4/7).

As discussed above, the present inventors have previously shown that PLD2 and AQP3 colocalize in caveolin-rich membrane microdomains in keratinocytes. In addition, PLD-mediated PG synthesis is stimulated by elevated extracellular calcium levels in keratinocytes as shown, and it appears that AQP3 provides glycerol to PLD2 for the transphosphatidylation reaction to produce PG. Since in lung cells AQP3 is inhibited by acidic medium, whether a medium of low pH would inhibit glycerol uptake and PG synthesis was investigated. Keratinocytes were incubated for 24 hours with control SFKM (25 μM Ca$^{2+}$) or SFKM containing 125 μM Ca$^{2+}$ prior to measurement of [$^3$H]glycerol uptake and [$^{14}$C]PG production in SFKM of pH 4 or 7.4. As shown in FIG. 13A, 125 μM Ca$^{2+}$ significantly stimulated glycerol uptake in control medium. Low pH medium significantly inhibited glycerol uptake both under basal conditions and upon stimulation with the intermediate calcium concentration (FIG. 13A). Similarly, pH 4 medium significantly inhibited radiolabeled PG synthesis after a 10-minute incubation with [$^{14}$C]glycerol both in cells incubated with control medium and 125 μM Ca$^{2+}$ medium (FIG. 13B). In order to ensure that the inhibition of glycerol uptake and/or PG production by pH 4 medium was not related to toxicity, some cells were also preincubated for 5 minutes with pH 4 medium prior to measurement of glycerol uptake or PG synthesis in control pH 7.4 medium (pH 4/7). Preincubation with pH 4 medium had essentially no effect on glycerol uptake or PG production (FIG. 13).

Figure 14:
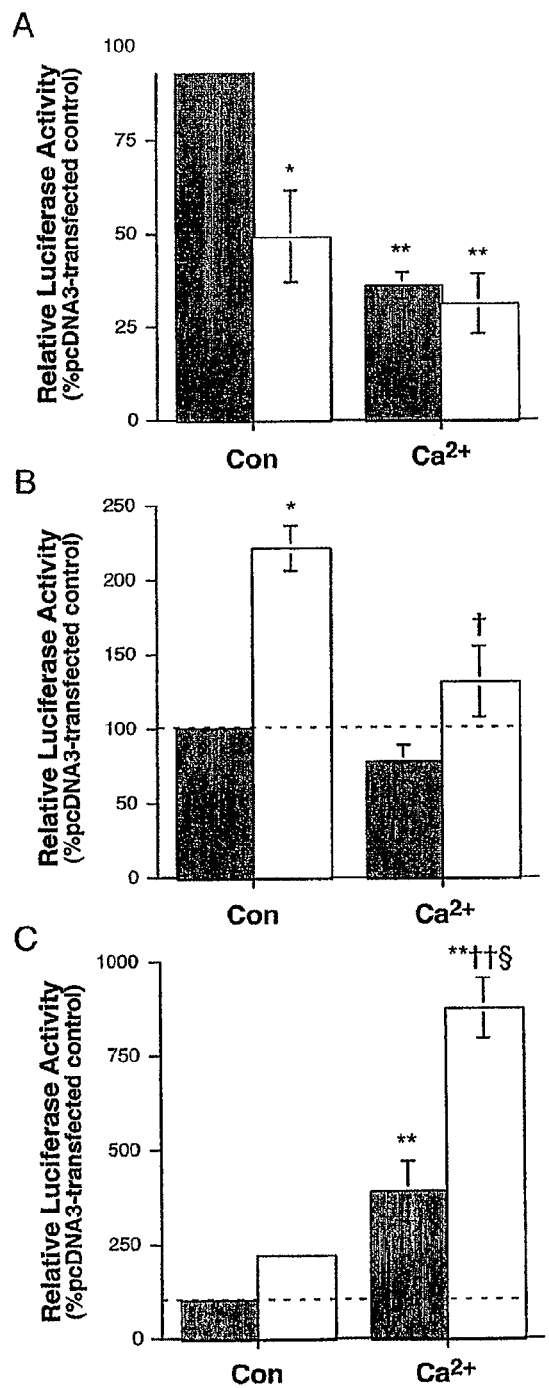
FIGS. 14A-C are bar graphs demonstrating that AQP3 overexpression decreases keratin 5 promoter activity, increases keratin 10 promoter activity and enhances the effect of elevated [Ca$^{2+}$], on involucrin promoter activity. Primary keratinocytes were co-transfected with pcDNA3 vector alone (control) or the vector possessing AQP3 and (A) the keratin 5 promoter/reporter gene construct or (B) the involucrin promoter/reporter gene constructs (and pRL-SV40 for normalization purposes) using TransIT-Keratinocyte as described by the manufacturer. After 24 hours, cells were re-fed with medium containing 25 μM (control) or 1 HiM-Ca$^{2+}$ for an additional 24 hours. Luciferase activity was then measured using a Dual Luciferase kit as directed by the manufacturer. Activity is expressed relative to the pcDNA3-transfected control cells and represents the mean±SEM of three experiments performed in triplicate; *p<0.01, **p<0.001 versus the control (untreated pcDNA3 vector) value, †p<0.01, ††p<0.001 versus the AQP3-transfected value under control conditions, and §p<0.001 versus the Ca$^{2+}$-treated pcDNA3 vector control value.
Figure 15:
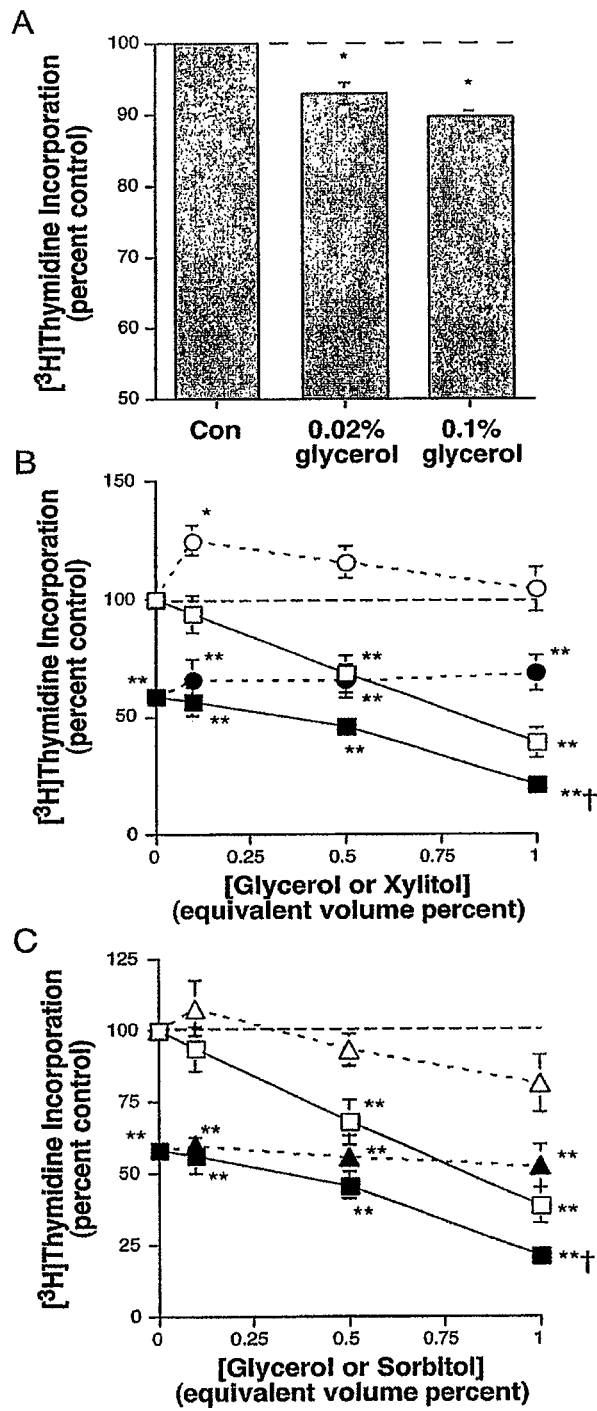
FIGS. 15A-B illustrate that glycerol, but not xylitol or sorbitol, inhibits DNA synthesis and enhances the inhibitory effect of an elevated extracellular Ca$^{2+}$ concentration. (A) Near-confluent keratinocytes were incubated for 24 hours with 0.02 or 0.1% glycerol and DNA synthesis measured as the incorporation of [$^3$H] thymidine incorporation into DNA. (B) Near-confluent keratinocytes were incubated for 24 hours with the indicated concentrations of glycerol (G, squares) or equivalent concentrations of xylitol (X, circles) in SFKM containing 25 μM (control; open symbols) or 125 μM Ca$^{2+}$ (Ca$^{2+}$; closed symbols). (C) Near-confluent keratinocytes were incubated for 24 hours with the indicated concentrations of glycerol (G) or equivalent concentrations of sorbitol (S, triangles) in SFKM containing 25 μM (control; open symbols) or 125 μM Ca$^{2+}$ (Ca$^{2+}$; closed symbols) for 24 hours. [$^3$H]Thymidine incorporation into DNA was then determined. Values represent the means±SEM of 4 to 5 separate experiments performed in duplicate; *p<0.05, **p<0.01 versus the control value, †p<0.05 versus the value in the presence of Ca$^{2+}$ alone. (D) Primary keratinocytes were co-transfected with pcDNA3 vector alone (control) or the same vector possessing AQP3 and the keratin 5 promoter/reporter construct (and pRL-SV40 for normalization purposes) using TransIT-Keratinocyte as described by the manufacturer. After 24 hours cells were refed with medium containing no addition (control) or 0.2% glycerol for an additional 24 hours. Luciferase activity was then measured using a Dual Luciferase kit as directed by the manufacturer. Activity is expressed relative to the pcDNA3-transfected control cells and represents the mean±SEM of 5 experiments performed in triplicate; *p<0.05, p<0.01, *p<0.001 versus the control (untreated pcDNA3 vector) value; †p<0.05 versus the AQP3-transfected value under control conditions. (E) Near-confluent keratinocytes were incubated for 24 hours with the indicated concentrations of PG, prepared via bath sonication of PG in SFKM, in 25 μM Ca$^{2+}$-containing medium (control) or medium containing 125 μM Ca$^{2+}$. Cells were harvested and subject to western analysis using an anti-involucrin antibody (Covance) and the LiCor Odyssey system. The blots were quantified using the Kodak molecular imaging software. Values represent the mean±SEM of 3-4 separate experiments performed in duplicate; *p<0.05, **p<0.01 versus the control value.
Figure 15:
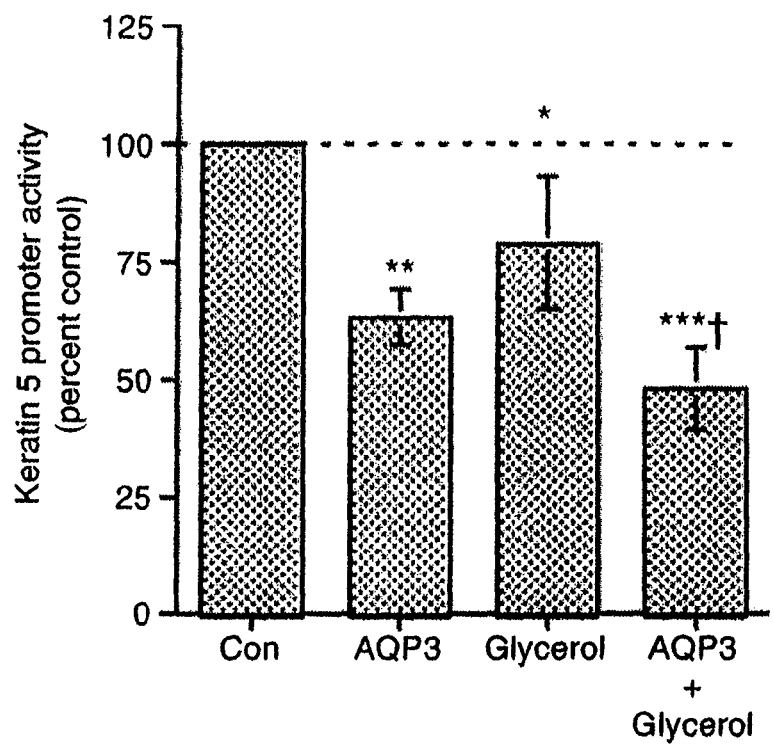
Figure 15:
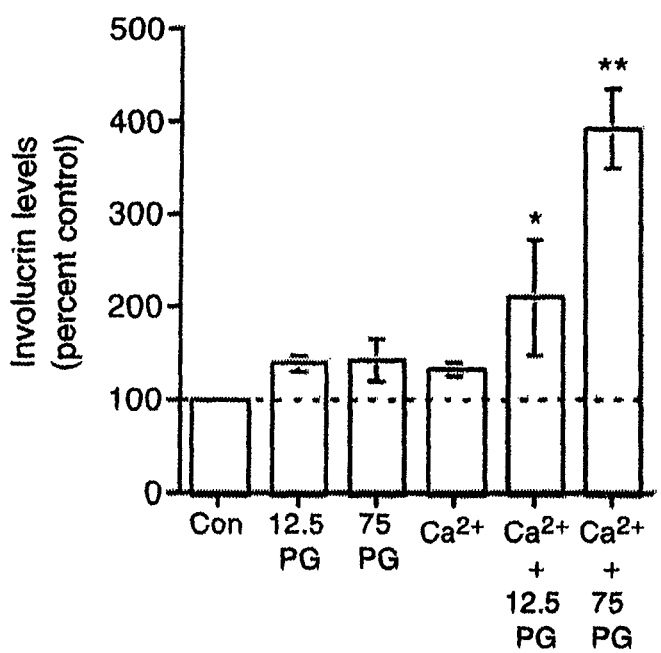

Co-expression of AQP3 Inhibits Keratin 5 Promoter Activity, Stimulates Keratin 10 Promoter Activity and Enhances the Effect of an Elevated Extracellular Calcium Level on Involucrin Promoter Activity Primary mouse epidermal keratinocytes can be difficult to transfect with high efficiency. To overcome this limitation, the cells were co-transfected with AQP3 or the empty vector and reporter constructs in which promoters for markers of keratinocyte proliferation or differentiation control luciferase expression as described by Dodd, et al. Since vectors are mixed thoroughly prior to transfection, cells that take up one vector can incorporate the other, allowing measurement of reporter luciferase activity only in cells that also possess AQP3 or the empty vector. Whereas keratin 5 expression characterizes basal proliferating keratinocytes, keratin 10 and involucrin mark the differentiating spinous cells, with keratin 10 serving as a marker for early differentiation and involucrin as a marker for intermediate differentiation. FIG. 14A illustrates the effect of AQP3 co-expression on keratin 5 promoter activity under basal conditions and after a 24-hour incubation with the differentiating agent, 1 mM calcium. AQP3 co-expression induced a significant decrease (to 49±12% of the empty vector-transfected control) in keratin 5 promoter activity. Calcium (1 mM) also inhibited keratin 5 promoter activity (by 64%) and there was no significant additional effect of AQP3 co-expression. On the other hand, AQP3 co-expression stimulated keratin 10 promoter activity (FIG. 14B). Treatment with 1 mM calcium inhibited keratin 10 expression by 22%, and this effect was partially reversed by AQP3 co-expression. As a differentiating agent, 1 mM calcium might be expected to increase keratin 10 promoter activity; however, such high calcium concentrations drive keratinocytes towards later differentiation and actually reduce the expression of early differentiation markers. Finally, AQP3 co-expression had no significant effect on involucrin promoter activity alone but enhanced the stimulation induced by 1 mM calcium (FIG. 14C). These results are consistent with AQP3 co-expression promoting early keratinocyte differentiation. Glycerol and 1,2-Propylene Glycol, but not Xylitol or Sorbitol, Inhibit DNA Synthesis The AQP3 and PLD2 appear to colocalize to provide glycerol for use by PLD2 in the transphosphatidylation reaction to generate PG, which then acts to promote early keratinocyte differentiation. This suggests that increasing the delivery of glycerol through the AQP3 channel can also trigger early differentiation. Since one of the first hallmarks of early differentiation is exit from the cell cycle and a reduction in DNA synthesis, the effect of exogenous glycerol (to enhance flux through the channel) on [$^3$H]thymidine incorporation into DNA, a measure of DNA synthesis, was investigated. As shown in FIG. 15A concentrations of glycerol as low as 0.02% (=2.73 mM) significantly inhibited keratinocyte DNA synthesis. The effects of higher concentrations of glycerol were also investigated. However, because osmotic stress regulates keratinocyte function, to control for any osmotic effects of glycerol equivalent concentrations of two other osmolytes, xylitol and sorbitol, were also used as controls. As shown in FIG. 15B, glycerol at concentrations from 0.1 to 1% inhibited DNA synthesis and enhanced the inhibitory effect of 125 µM $Ca^{2+}$. On the other hand, xylitol had no significant effect on basal or 125 µM $Ca^{2+}$-inhibited DNA synthesis. Similarly, we observed no significant effect of sorbitol on either control or 125 µM $Ca^{2+}$-reduced [$^3$H]thymidine incorporation into DNA (FIG. 15C).

To determine whether glycerol inhibition of proliferation in keratinocytes was related to AQP3, the effect of AQP3 transfection, with and without added glycerol, on keratin 5 promoter activity was examined. As shown in FIG. 15D, transfection of keratinocytes with AQP3 inhibited keratin 5 promoter activity relative to control (transfection with empty vector). Glycerol (0.2%) induced a small but significant reduction in keratin 5 promoter activity (about a 9% reduction) Keratinocytes transfected with AQP3 and treated with glycerol (0.2%) showed an enhanced inhibition of keratin 5 promoter activity (about a 47% reduction). This result suggests that AQP3 expression enhanced the inhibitory effect of glycerol on the basal-like phenotype of keratinocytes.

PG was also examined for its ability to stimulate a marker of keratinocyte differentiation. Keratinocytes were treated with or without PG liposomes in 25 uM $Ca^{2+}$ (control) or 125 uM $Ca^{2+}$-containing medium for 24 hours and cell lysates were analyzed for involucrin protein levels (normalized to actin as a loading control) (FIG. 15E). PG liposomes lone and 125 uM $Ca^{2+}$ had not significant effect on involucrin protein levels. However, the combination of PG liposomes and moderately elevated $Ca^{2+}$ produced a significant increase in involucrin protein levels. This result suggests that the AQP3, PLD2, glycerol and PG signaling module participates in early keratinocyte differentiation but that later differentiation requires the provision of additional signals (which may be triggered by the early differentiation pathway).

In studies of the AQP3 null mutant mouse, glycerol, but not xylitol or 1,2-propylene glycol (or 1,3-propylene glycol), could correct the epidermal phenotype of this knockout model. Therefore, 1,2-propylene glycol was also tested for its ability to inhibit DNA synthesis basically and upon differentiation with 125 µM $Ca^{2+}$. The effect of 1,2-propylene glycol was analogous to that of glycerol, exhibiting dose dependent inhibition of [$^3$H]thymidine incorporation under control (25 µM $Ca^{2+}$) conditions and upon differentiation with 125 µM $Ca^{2+}$ (FIG. 16A). Also shown in FIG. 16B are the structures of glycerol and 1,2-propylene glycol to demonstrate their similarity.

PG Liposomes Inhibit DNA Synthesis in Rapidly Dividing Keratinocytes and Stimulate Transglutaminase Activity It is further believed that direct provision of PG itself will also trigger early differentiation. Providing PG in the form of liposomes directly to keratinocytes was found to inhibit DNA synthesis in highly proliferative cells (FIG. 17A). Maximal inhibition was observed at 25 µg/mL with a plateau from 50 to 100 µg/mL. This effect is not likely to represent toxicity since morphologic changes characteristic of cell death were not observed (data not shown). There existed the possibility that PG liposomes inhibited DNA synthesis nonspecifically. To test this hypothesis, keratinocytes were treated with liposomes from dioleoyl-phosphatidylpropanol (PP) and DNA synthesis was determined as discussed above. As above, PG liposomes inhibited DNA synthesis; however PP liposomes showed no impact on DNA synthesis in highly proliferative keratinocytes (FIG. 17C). It was also shown that dipalmitoyl-PP did not affect DNA synthesis in highly proliferative keratinocytes (data not shown).

In addition, PG liposomes induced a dose-dependent trend towards increased transglutaminase activity, a marker of late keratinocyte differentiation (FIG. 17B).

PG Liposomes Stimulate DNA Synthesis in Slowly Proliferating Cells

Figure 18:
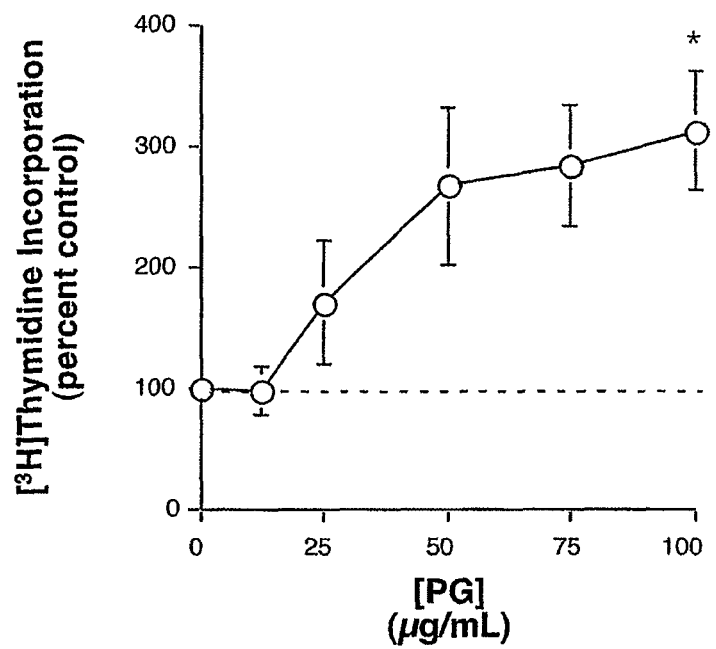
FIG. 18 shows that PG liposomes increase DNA synthesis in growth-inhibited keratinocytes. Confluent keratinocytes were treated for 24 hours with the indicated concentrations of phosphatidylglycerol (PG), prepared via bath sonication of PG in serum-free keratinocyte medium. [$^3$H]Thymidine incorporation into DNA was then determined as above. [$^3$H]Thymidine incorporation into DNA under control conditions was 12,880±1,040 cpm/well. Values represent the means±SEM of 3 separate experiments performed in duplicate; *$p<0.01$, **$p<0.001$ versus the control value.

Additional evidence for a lack of toxicity was provided by the observed effects of the PG liposomes on keratinocytes exhibiting reduced proliferation presumably as the result of contact inhibition. Thus, if PG liposomes were applied to keratinocytes with decreased proliferative capacity (as indicated by reduced [$^3$H]thymidine incorporation into DNA under control conditions), DNA synthesis was stimulated in a dose-dependent manner, with a half-maximal effect at a concentration of approximately 35 µg/mL and a maximal stimulation at 100 µg/mL (FIG. 18). This result suggests that PG has the capacity to normalize keratinocyte proliferation, inhibiting the proliferation of rapidly dividing cells and increasing proliferation in a setting of reduced growth.

Discussion

The ability of PLD to utilize glycerol in a transphosphatidylation reaction to synthesize PG, and the interaction between PLD2, and AQP3, suggested a mechanism by which glycerol could reach this isoenzyme for the transphosphatidylation. This inhibition of the glycerol uptake function of AQP3 can reduce PG synthesis as well. FIG. 13 shows that acidic medium induces a concomitant decrease in 125 µM $Ca^{2+}$-elicited glycerol uptake and PG synthesis. However, since other aquaporins are capable of transporting glycerol, such as aquaporin-9, and are expressed by keratinocytes these other aquaglyceroporins may also contribute to glycerol uptake and PG synthesis in keratinocytes.

It is believed that the PG synthesized by the PLD2/AQP3 signaling module serves as a lipid messenger to regulate keratinocyte and epidermal function. AQP3 null mutant mice exhibit an epidermal phenotype that can be corrected by glycerol but not other osmotically active agents. The present co-expression studies suggest that AQP3 promotes early keratinocyte differentiation: AQP3 decreased the promoter activity of keratin 5 (FIG. 14A), a marker of the basal proliferative layer. Downregulation of keratin 5 expression characterizes the transition of basal keratinocytes into the first suprabasal cells in the spinous layer. Also characteristic of spinous keratinocytes is an increase in the expression of keratin 10; co-expression of AQP3 increased keratin 10 promoter activity (FIG. 14B). High calcium levels may propel keratinocytes past early differentiation steps to a later differentiation stage, resulting in a slight reduction in keratin 10 promoter activity (FIG. 14B). As keratinocytes proceed to migrate up through the multiple spinous layers, they begin to express involucrin. Although AQP3 co-expression alone did not significantly increase involucrin promoter activity, AQP3 did enhance the effect of another differentiating agent, elevated extracellular calcium concentration on the promoter activity of this intermediate differentiation marker (FIG. 14C). It should be noted that it seems unlikely that AQP3 is directly affecting the promoter activities of these various markers, i.e. via interactions with other transcription factors and/or the promoters themselves. Rather, the results are consistent with AQP3 expression inducing an early differentiation phenotype, and that the differentiation status of the cells then controls the activities of these promoters.

Figure 16:
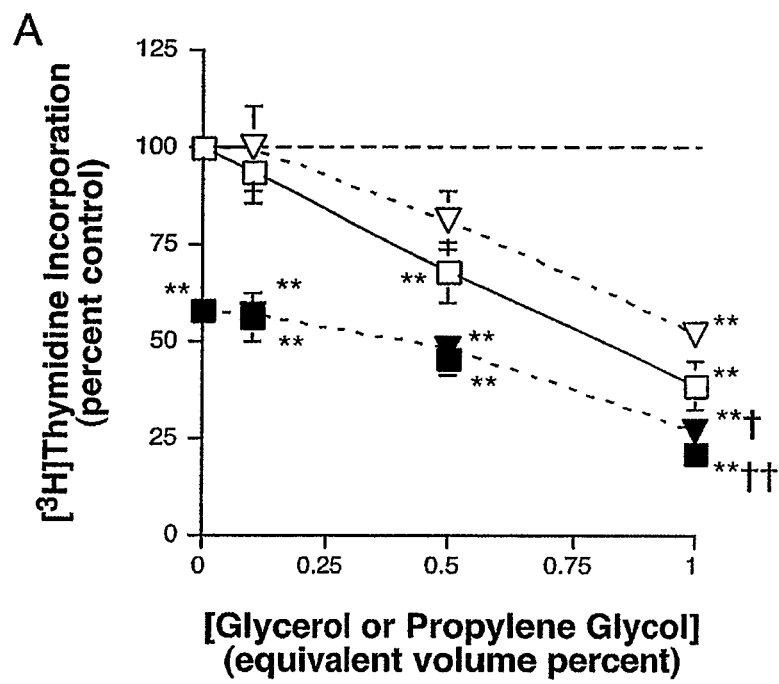
FIG. 16 demonstrates that 1-,2-propylene glycol (1,2-propanediol) inhibits DNA synthesis and enhances the inhibitory effect of an elevated extracellular Ca$^{2+}$ concentration. (A) Near-confluent keratinocytes were incubated for 24 hours with the indicated concentrations of glycerol (G, squares) or equivalent concentrations of 1,2-propylene glycol (1,2-propanediol, triangles) in SFKM containing 25 μM (control; open symbols) or 125 μM Ca$^{2+}$ (Ca$^{2+}$; closed symbols). [$^3$H] Thymidine incorporation into DNA was then determined as in [3]. Values represent the means±SEM of 3 to 5 separate experiments performed in duplicate; *p<0.05, **p<0.01 versus the control value, †p<0.05 versus the value in the presence of $Ca^{2+}$ alone. (B) The structures of glycerol and 1,2-propylene glycol demonstrate the similarity of their configuration.
Figure 16:
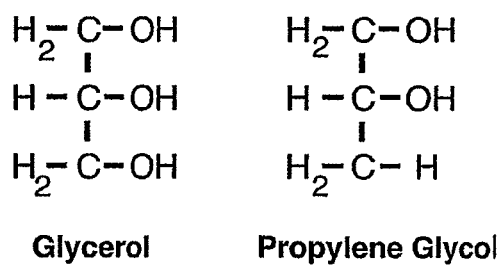

It is believed that increasing glycerol influx will promote PG synthesis and promote this early differentiation phenotype, a primary event of which is growth arrest. Indeed, glycerol inhibited DNA synthesis and this inhibition was not reproduced by equivalent concentrations of two other osmotically active compounds, xylitol and sorbitol (FIG. 15), suggesting that the inhibition was not the result of increased osmolality. Interestingly, 1,2-propylene glycol (1,2-propanediol) produced an essentially identical effect as glycerol on DNA synthesis (FIG. 16). It is believed that the phospholipid formed by transphosphatidylation with 1,2-propylene glycol (PG missing the hydroxy group on the terminal carbon) is similar enough to PG to activate PG effector enzymes.

Figure 17:
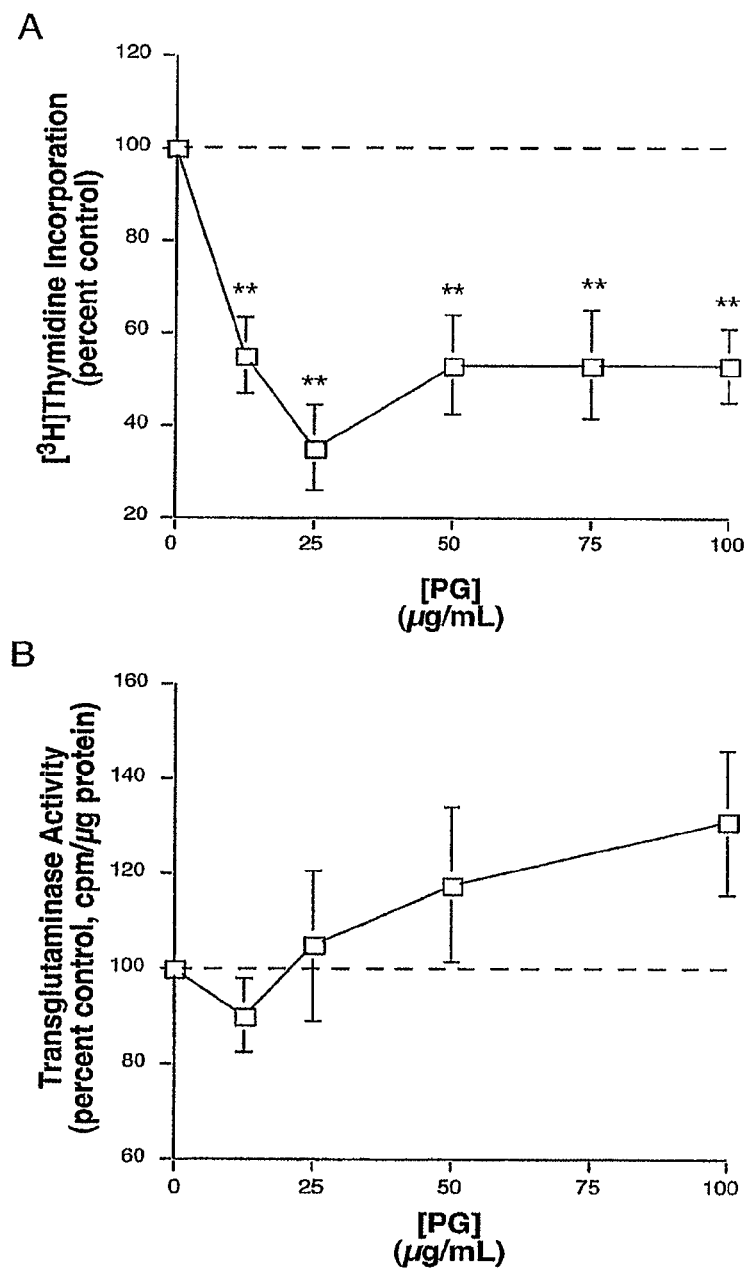
FIG. 17 illustrates that PG liposomes, but not PP liposomes, inhibit DNA synthesis in proliferating keratinocytes and PG liposomes dose-dependently stimulate transglutaminase activity. (A) Near-confluent keratinocytes were treated for 24 hours with the indicated concentrations of phosphatidylglycerol (PG), prepared via bath sonication of PG in serum-free keratinocyte medium. [$^3$H]Thymidine incorporation into DNA was then determined. [$^3$H]Thymidine incorporation into DNA in the control was 85,550±5,730 cpm/well. Values represent the means±SEM of 7-9 separate experiments performed in duplicate; *$p<0.01$, **$p<0.001$ versus the control value. (B) Near-confluent keratinocytes were treated for 24 hours with the indicated concentrations of phosphatidylglycerol (PG), prepared via bath sonication of PG in serum-free keratinocyte medium. Transglutaminase activity was then determined. Values represent the means±SEM of separate experiments performed in duplicate; the increasing doses exhibited a significant stimulatory trend; *$p<0.05$. (C) Near-confluent keratinocytes were treated for 24 hours with the indicated concentrations of phosphatidylglycerol (PG) or phosphatidylpropanol (PP), prepared via bath sonication of PG or PP in serum-free keratinocyte medium. [$^3$H]Thymidine incorporation into DNA was then determined. Values represent the means±SEM of 5-6 separate experiments performed in duplicate; *$p<0.05$, **$p<0.001$ versus the control value.
Figure 17:
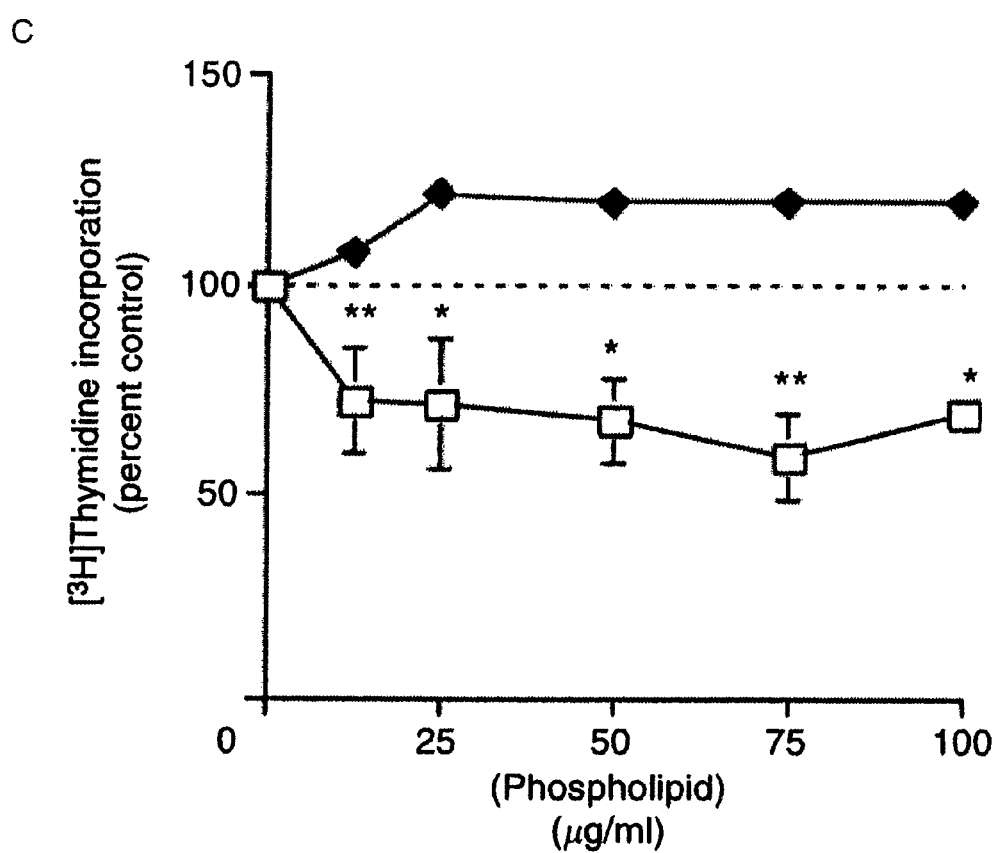

If glycerol functions to alter keratinocyte proliferation by serving as a substrate for PG formation, then direct provision of PG would also inhibit DNA synthesis. Indeed, in rapidly growing cells (as determined by high [$^3$H]thymidine incorporation into DNA under basal conditions), PG dose-dependently decreased DNA synthesis (FIG. 17). This effect did not seem to be the result of non-specific toxicity as no morphological correlates of toxicity were observed (data not shown). In addition, increasing PG doses also showed a tendency to stimulate transglutaminase activity, a marker of late keratinocyte differentiation. However, unexpectedly, in keratinocytes that exhibited reduced DNA synthesis, likely as the result of contact inhibition, PG dose dependently stimulated DNA synthesis (FIG. 18). The mechanism of this biphasic response is unknown (although possibilities are discussed below), but in cases where the epidermis is hyperproliferative, PG liposomes would be expected to inhibit keratinocyte growth, whereas under conditions of too little proliferation (e.g., with age) the liposomes should increase growth. Thus, the results suggest that PG liposomes might be an ideal treatment to normalize skin function under both pathological and physiological conditions.

The effector enzyme for the PG signal is also unknown; however, possibilities include PG-sensitive protein kinases such as protein kinase C-II, PKC-, and Pk-P. Alternatively, PG may be incorporated into the plasma membrane and/or specific microdomains and influence membrane protein assembly and/or microdomain function. As an example, PG is utilized in photosystem assembly in thylakoid membranes of cyanobacteria and spinach. PG is also a precursor of cardiolipin (=diphosphatidylglycerol), and both PG and cardiolipin are important in mitochondrial function. Cardiolipin binds to cytochrome c, and oxidation of this lipid is thought to allow release of cytochrome c from the mitochondria, an event that can initiate apoptosis. In addition, the incubation of both cardiolipin and PG with depleted mitochondria can partially restore their membrane potential and this opposes cytochrome c release and apoptosis. Indeed, PG can inhibit apoptosis in retinal epithelial cells. Thus, PG may induce growth inhibition of rapidly proliferating keratinocytes (as in FIG. 17A) through activation of a protein kinase pathway, whereas this phospholipid may promote proliferation in inhibited cells (as in FIG. 18) by improving mitochondrial function and energy production. The observed upregulation of AQP3 expression by exposure to ultraviolet light is believed to be a cellular response to promote PG production, mitochondrial health and recovery from the stress of the irradiation. Thus, the novel signaling module consisting of AQP3, PLD2, glycerol and PG represents a mechanism for the beneficial effects of glycerol in skin. Further, the present results indicate that this module is an important modulator of keratinocyte growth and differentiation in vitro and in vivo and provides novel treatments for various skin disorders and/or conditions.

Example 3

Glycerol and Phosphatidylglycerol Accelerate Wound Healing

Figure 19:
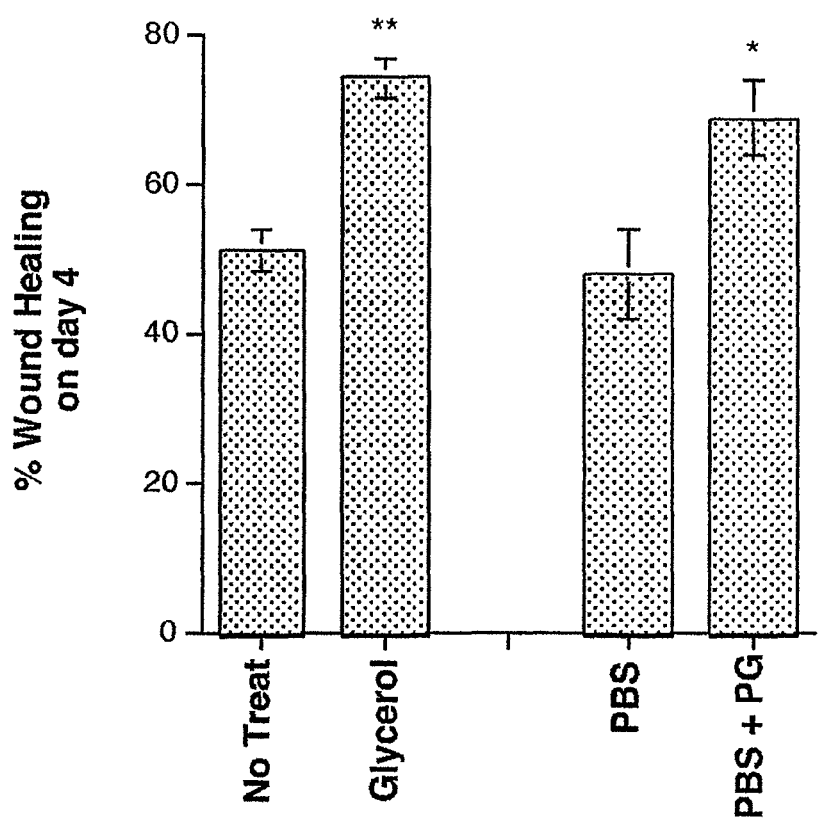
FIG. 19 is a bar graph showing the effect of glycerol and phosphatidylglycerol on the rate of wound healing.

This example presents recent data on the effects of glycerol and phosphatidylglycerol treatment on wound healing obtained in ICR CD1 mice. Two full-thickness skin punch biopsies of ~4 mm were made on the backs of a total of sixteen mice. For each mouse, one wound was either (a) untreated, (b) treated with 2M glycerol in water, (c) treated with phosphate-buffered saline lacking divalent cations (PBS-), or (d) PBS-containing 100 μg/mL phosphatidylglycerol (sonicated to form liposomes). The rate of wound healing was then followed over four days by digital photography and computer image analysis. Shown in FIG. 19, as a bar graph, is the percentage of wound healing on day 4, relative to day 1, for each of the four groups. Glycerol treatment improved the rate of wound healing, as anticipated. More importantly, PG liposomes also increased the rate of wound healing, and this improvement was statistically significant. These results validate the idea of the importance of PG in skin function.

Example 4

This example presents evidence that various PG species and functional derivatives of PG are capable of modulating keratinocyte differentiation and keratinocyte and epidermal function.

The data presented herein used egg-derived PG that predominately included palmitic acid and oleic acid as the major fatty acid molecules in the $R_1$ and $R_2$ positions (derived from the phosphatidylcholine moiety). However, as discussed herein, various species of PG may be used that contain a variety of fatty acid molecules in the $R_1$ and $R_2$ positions.

The fatty acid molecules in the $R_1$ and $R_2$ positions may be saturated, monounsaturated or polyunsaturated. The nature of the fatty acid molecules at the $R_1$ and $R_2$ positions may be the same or may be different; for example, one fatty acid molecule may be myristic acid (a 14 carbon saturated fatty acid molecule) and one fatty acid may be vaccenic acid (a 18 carbon monunsaturated fatty acid molecule). In one embodiment, the PG molecule contains fatty acids without unsaturated bonds, such as, but not limited to, myristic or palmitic. In an alternate embodiment, the PG molecule contains at least one fatty acid with one unsaturated bond, such as but not limited to, oleic or palmitoleic. In another embodiment, the PG molecule contains at least one fatty acid with at least two unsaturated bonds, such as but not limited to, linoleic or arachidonic. The fatty acid molecules in the $R_1$ and $R_2$ positions may contain from 4-28 carbon atoms and from 0-6 unsaturated bonds. Exemplary fatty acid molecules, include, but are not limited to, butyric (4:0), valeric (5:0), caproic (6:0), caprylic (8:0), capric (10:0), lauric (12:0), myristic (14:0), myristoleic (14:1, cis-9), palmitic (16:0), palmitoleic (16-1,9-cis), stearic (18:0), oleic (18:1, 11-cis), vaccenic (18:1, 11-trans), linoleic (18:2, 9-cis 12-cis), -γ-linolenic (18:3, 6-cis 9-cis 12-cis), α-linolenic (18:3, 9-cis 12-cis 15-cis), arachidic (20:0), arachidonic (20:4, 5-cis, 8-cis, 11-cis 14-cis), eicosapentaenoic (20:5, 5-cis 8-cis 11-cis 14-cis 17-cis), behenic (22:0), erucic (22:1, 13-cis), docosahexaenoic (22:6, 4-cis 7-cis 10-cis 13-cis 16-cis 19-cis), lignoceric (24:0) and cerotic (26:0).

Furthermore, various headgroups may be incorporated to produce functional derivatives of PG through the use of primary alcohol substrates other than glycerol in the transphosphatidylation reaction to produce the corresponding phosphatidylalcohol.

This example demonstrates that the nature of the fatty acid molecule incorporated into the PG or functional derivative thereof and the nature of the headgroup incorporated into functional derivatives of PG can impact the activity of the PG or functional derivative thereof in modulating keratinocyte function.

Experimental Procedures
Keratinocyte Preparation and Cell Culture

Keratinocytes were prepared from ICR CD-1 outbred mice as described in

Example 2

Assay of DNA Synthesis

[$^3$H]Thymidine incorporation was used as a measure of DNA synthesis and was performed as described in Example 2. Liposomes containing PG and functional derivatives thereof were prepared by bath sonication as described in Example 2, with the exception that different concentrations of material were employed.

Statistics

Experiments were performed a minimum of three times as indicated. Values were analyzed for statistical significance by analysis of variance (ANOVA) with a Student-Newmann-Keuls post-hoc test using Instat (GraphPad Software, San Diego, Calif.).

Results
Dilinoleoyl-PG (DLPG), Palmitoyl-Arachidonoyl-PG (PAPG) and Palmitoyl-Linoleoyl-PG (PLPG) Inhibit DNA Synthesis in Rapidly Dividing Keratinocytes Various PG species containing selected fatty acid molecules at the $R_1$ and $R_2$ positions were tested for their ability to inhibit DNA synthesis in rapidly dividing keratinocytes. Providing DLPG, PAPG and PLPG in the form of liposomes directly to keratinocytes was found to inhibit DNA synthesis in a dose dependent manner in highly proliferative cells (FIG. 20A). DLPG, PAPG and PLPG inhibited DNA synthesis at least as strongly as egg-derived PG. DLPG (18:2-18:2), PAPG (16:0-20:4) and PLPG (16:0-18:2) each contain at least one fatty acid with at least two unsaturated bonds (i.e., a polyunsaturated fatty acid), For DLPG, maximal inhibition was observed at 100 μg/mL with inhibition observed at concentrations as low as 6.25 μg/mL. For PAPG, maximal inhibition was observed at 100 μg/mL with inhibition observed at concentrations as low as 12.5 μg/mL. For PLPG maximal inhibition was observed at 100 μg/mL with inhibition observed at concentrations as low as 50 μg/mL.

In addition to DLPG, PAPG and PLPG, palmitoyl-oleoyl-PG (POPG, 16:0-18:1) showed moderate inhibition of DNA synthesis (FIG. 20A). POPG exhibited inhibition only at the highest concentration tested (100 μg/mL).

As discussed above, these effects are not likely to represent toxicity since morphologic changes characteristic of cell death were not observed (data not shown).

Furthermore, soy-derived PG was a more potent inhibitor of DNA synthesis than egg-derived PG. On average, soy-derived PG (from Avanti Polar Lipids) contains 59% 18:2, 13% 18:1 and 17% 16:0 fatty acids (plus other species at less than 10%) while egg-derived PG (from Avanti Polar Lipids) contains 34% 16:0, 32% 18:1, 18% 18:2 and 11% 18:0 fatty acids (plus other species at less than 10%). POPG, which was a weaker inhibitor, contains one fatty acid with one unsaturated bond and one fatty acid with no unsaturated bonds. DOPG also followed this trend and showed no inhibition of DNA synthesis.

These data show that the fatty acid composition of the PG species can impact its ability to modulate keratinocyte differentiation (for example in this case by stimulating differentiation) and that the degree of unsaturation in the fatty acid composition of the PG species can impact the ability of PG species to inhibit DNA synthesis in rapidly proliferating keratinocytes.

Figure 20B:
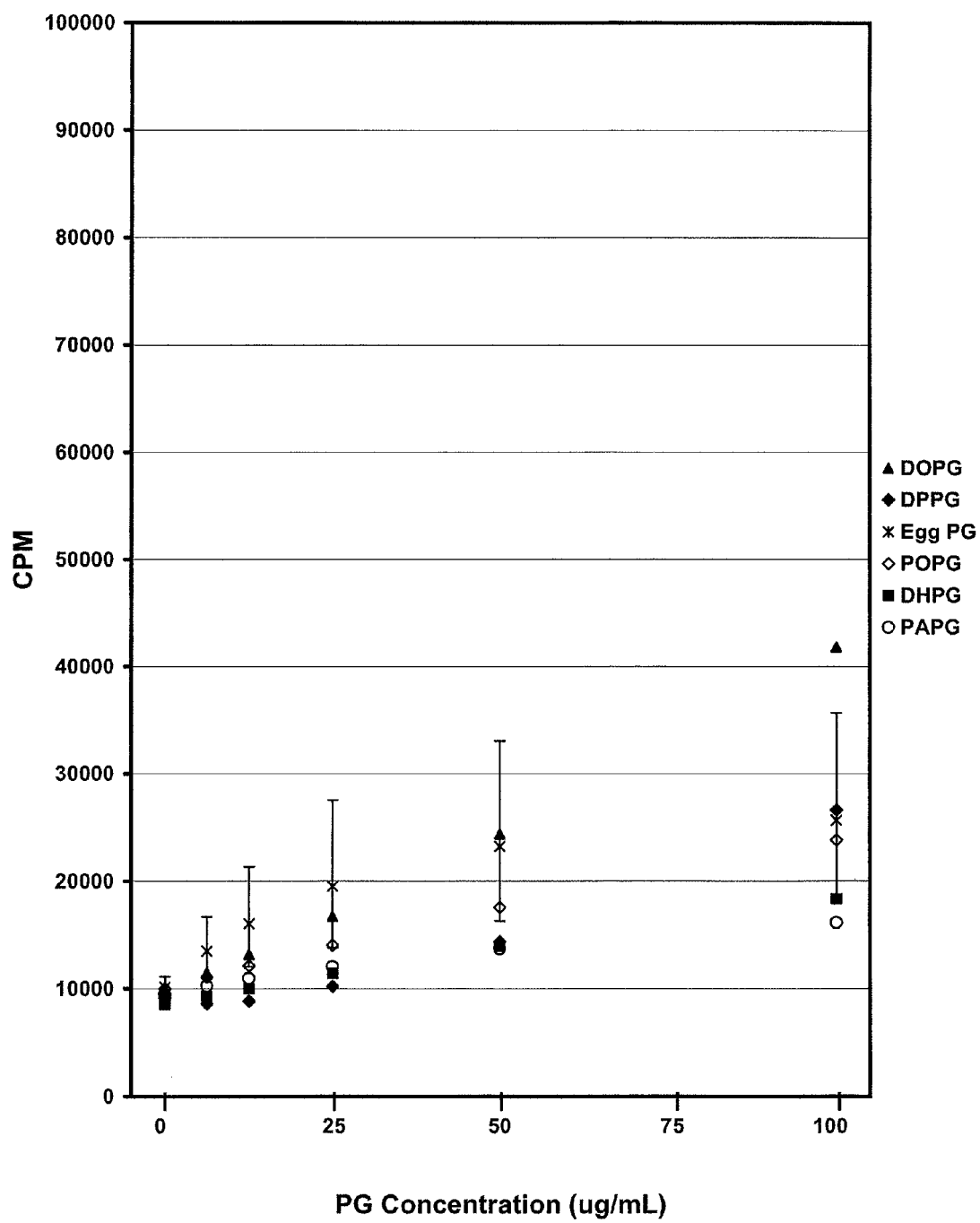
FIG. 20 illustrates that PG liposomes containing selected fatty acid molecules at the $R_1$ and $R_2$ positions impact the ability of PG to normalize keratinocyte proliferation. (A) Rapidly proliferating keratinocytes were treated for 24 hours with the indicated concentrations and species of phosphatidylglycerol (PG), prepared via bath sonication of PG in serum-free keratinocyte medium. [$^3$H]Thymidine incorporation into DNA was then determined. Values represent the means (±SEM for egg-derived PG) of at least four separate experiments. PG species tested were DHPG (dihexanoyl-PG, 6:0-6:0), DPPG (dipalmitoyl-PG, 16:0-16:0), DOPG (dioleoyl-PG, 18:1-18:1), DSPG (distearoyl-PG, 18:0-18:0), POPG (palmitoyl-oleoyl-PG, 16:0-18:1), egg-derived PG, PLPG (palmitoyl-linoleoyl-PG, 16:0-18:2), soy-derived PG, PAPG (palmitoyl-arachidonoyl-PG, 16:0-20:4) and DLPG (dilinoleoyl-PG, 18:2-18:2). (B) Slowly proliferating keratinocytes were treated for 24 hours with the indicated concentrations and species of phosphatidylglycerol (PG), prepared via bath sonication of PG in serum-free keratinocyte medium. [$^3$H]Thymidine incorporation into DNA was then determined. Values represent the means (±SEM for egg-derived PG) of at least four separate experiments. PG species tested were DHPG (dihexanoyl-PG, 6:0-6:0), DPPG (dipalmitoyl-PG, 16:0-16:0), DOPG (dioleoyl-PG, 18:1-18:1), POPG (palmitoyl-oleoyl-PG, 16:0-18:1), egg-derived PG and PAPG (palmitoyl-arachidonoyl-PG, 16:0-20:4).

Dioleoyl-PG (DOPG) and Dipalmitoyl-PG (DPPG) Stimulate DNA Synthesis in Slowly Dividing Keratinocytes As discussed herein, PG is able to inhibit DNA synthesis in rapidly proliferating cells but stimulate DNA synthesis in slowly proliferating cells. Various PG species containing selected fatty acid molecules at the $R_1$ and $R_2$ positions were tested for their ability to stimulate DNA synthesis in slowly dividing keratinocytes. DOPG was shown to be a potent stimulator of DNA synthesis in slowly dividing keratinocytes (FIG. 20B). Stimulation was maximal at 100 μg/mL and could be observed as low as 12.5 μg/mL. DOPG stimulated DNA synthesis more potently than egg-derived PG.

DPPG stimulated DNA synthesis at approximately the same level as egg-derived PG, but the stimulatory effects were only apparent at concentrations of 50 μg/mL and higher. Dihexanoyl PG (DHPG, 6:0-6:0), POPG and PAPG were only mildly stimulatory. The stimulatory effect of certain PG liposomes also provides additional evidence for a lack of toxicity of the observed effects of the PG liposomes on keratinocytes exhibiting reduced proliferation presumably as the result of contact inhibition.

These data show that the fatty acid composition of the PG species can impact its ability to modulate keratinocyte differentiation (for example in this case by inhibiting differentiation). These results also show that PG species have the capacity to normalize keratinocyte proliferation, inhibiting the proliferation of rapidly dividing cells and increasing proliferation in a setting of slowly dividing cells, and that the nature of the fatty acid molecules incorporated into the PG species can impact this normalization of keratinocyte proliferation.

Figure 21A:
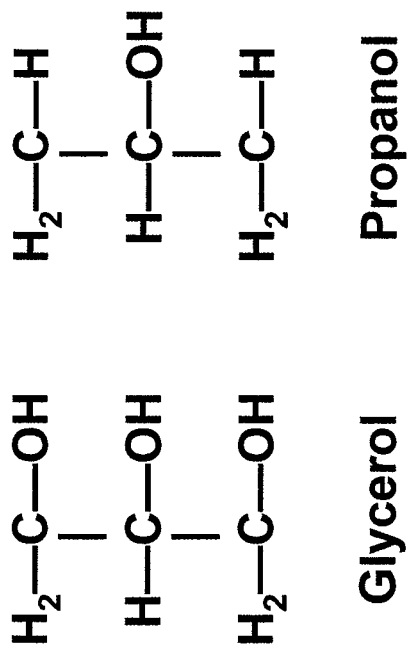
FIG. 21 shows the headgroup of the phosphatidylalcohol impacts the ability to normalize keratinocyte proliferation. (A) Shows the structure of glycerol and 1-propanol. (B) Near-confluent keratinocytes were treated for 24 hours with the indicated concentrations and species of phosphatidylglycerol (PG) or phosphatidylpropanol (PP), prepared via bath sonication of PG or PP in serum-free keratinocyte medium. [$^3$H]Thymidine incorporation into DNA was then determined. Species tested were dipalmitoyl-PG (DPPG, 16:0-16:0), dioleoyl-PG (DOPG, 18:1-18:1), dilinoleoyl-PG (DLPG, 18:2-18:2), dipalmitoyl-PP (DPPP, 16:0-16:0), dioleoyl-PP (DOPP, 18:1-18:1) and dilinoleoyl-PP (DLPP, 18:2-18:2). Values are expressed as percent of control (with control being no addition of any PG or PP species). Values represent the means±SEM of at least three separate experiments. The asterisk indicates a statistically significant difference from control ($p<0.05$).

The Identity of the Headgroup Impact the Ability of PG and Functional Derivatives Thereof to Modulate Keratinocyte Differentiation As discussed above, the identity of the headgroups may impact the ability of PG and functional derivatives of PG to modulate keratinocyte differentiation. Various headgroups may be incorporated through the use of primary alcohol substrates other than glycerol in the transphosphatidylation reaction to produce the corresponding phosphatidylalcohol. Selected phosphatidylalcohol molecules were produced using glycerol (to produce PG) or 1-propanol (to produce phosphatidylpropanol, PP) as the primary alcohol in the transphosphatidylation reaction. Various fatty acid molecules were also tested in each of the PG or PP derivatives produced to generate dipalmitoyl-PG (DPPG, 16:0-16:0), dioleoyl-PG (DOPG, 18:1-18:1), dilinoleoyl-PG (DLPG, 18:2-18:2), dipalmitoyl-PP (DPPP, 16:0-16:0), dioleoyl-PP (DOPP, 18:1-18:1) and dilinoleoyl-PP (DLPP, 18:2-18:2). The structure of glycerol and 1-propanol is shown in FIG. 21A.

Figure 21B:
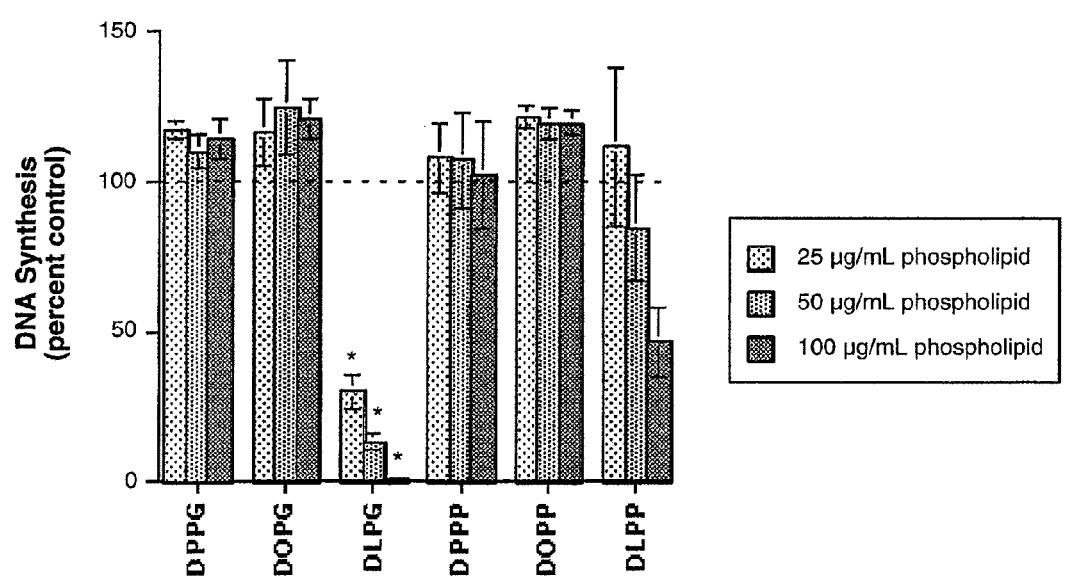

The above-identified species were tested for their ability to inhibit DNA synthesis in rapidly dividing keratinocytes (FIG. 21B). The results are expressed as percent of control (with control being no addition of any PG or PP species). As can be seen the identity of the headgroup and the nature of the fatty acid molecule impacted the ability of the species to inhibit DNA proliferation in rapidly dividing keratinocytes. In general, PG species were more effective in inhibiting DNA synthesis than PP species (compare DLPG to DLPP in FIG. 21B). DLPG inhibited DNA synthesis at the lowest concentration tested (25 µg/mL) while DLPP inhibited DNA synthesis only at the highest concentration tested (100 µg/mL). It should be noted that inhibition of DNA synthesis by DLPP was not statistically significant as compared to control.

Also, as shown in FIG. 20A, PG species containing dilinoleoyl as the fatty acid constituent were more effective in inhibiting DNA synthesis than PG species containing dipalmitoyl or dioleoyl as the fatty acid constituents (compare DLPG to DPPG and DOPG in FIG. 21B). The same was true of PP species (FIG. 21B); the data in FIG. 21B is consistent with the lack of effect of DPPP and DOPP shown in FIG. 17C.

These data show that the identity of the headgroup and the fatty acid composition can impact the ability of PG and functional derivatives of PG to modulate keratinocyte differentiation and can impact the ability of such species to inhibit DNA synthesis in rapidly proliferating keratinocytes. These results also show that PG as a headgroup is more effective in normalizing keratinocyte function (in this case inhibiting DNA synthesis in rapidly proliferating cells). Likewise, the data in FIG. 21 also confirm the nature of the fatty acid in the relevant species impacts the ability of PG and functional derivatives of PG to modulate keratinocyte differentiation. Consistent with the data in FIG. 20A, only those species incorporating fatty acid molecules with more than one unsaturated bond were effective in inhibiting DNA synthesis.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. AU such modifications and variations are intended to be included herein within the scope of this disclosure and protected by the following claims.

What is claimed:

1. A composition for treating a skin condition, the composition consisting essentially of an amount of a dilinoleoyl-phosphatidylglycerol optionally in a pharmaceutically acceptable carrier or excipient effective to treat the skin condition.

2. The composition of claim 1, wherein the skin condition is characterized by skin cell hyper-proliferation.

3. The composition of claim 1, wherein the skin condition is selected from at least one of the following: psoriasis, eczema, actinic keratosis, atopic dermatitis, basal cell carcinoma, non-melanoma skin cancer, and unregulated cell division.

4. A composition for treating a skin condition, the composition consisting essentially of a phosphatidylglycerol and glycerol, optionally in a pharmaceutically acceptable carrier or excipient, in an amount effective to treat the skin condition.

5. The composition of claim 1, wherein the dilinoleoyl-phosphatidylglycerol inhibits nucleic acid synthesis.

6. A composition for treating a skin condition, the composition comprising a lipid component, wherein the lipid component consists essentially of one or more of dilinoleoyl-phosphatidylglycerol, palmitoyl-arachidonyl-phosphatidyalglycerol, and palmitoyl-linoleoyl-phosphatidylglycerol, and wherein the lipid component is in an effective amount to treat the skin condition.

7. The composition of claim 6, further comprising glycerol.

8. The composition of claim 1, wherein the lipid component is in an amount effective to inhibit DNA synthesis by more than 50% when applied to dividing keratinocytes relative to a control.

9. The composition of claim 4, wherein the lipid component is in an amount effective to inhibit DNA synthesis by more than 50% when applied to dividing keratinocytes relative to a control.

10. The composition of claim 6, wherein the lipid component is in an amount effective to inhibit DNA synthesis when applied to skin cells by more than 50% relative to a control.

11. A liposome composition for treating a skin condition, the liposome composition comprising an effective amount of liposomes consisting essentially of a lipid selected from the group consisting of dilinoleoyl-phosphatidylglycerol, palmitoyl-arachidonyl-phosphatidyalglycerol, and palmitoyl-linoleoyl-phosphatidylglycerol, to inhibit DNA synthesis of dividing keratinocytes relative to a control.

12. The liposome composition of claim 11, further comprising glycerol.

* * * * *